(12) United States Patent
Susilo

(10) Patent No.: US 7,396,826 B2
(45) Date of Patent: Jul. 8, 2008

(54) PHARMACEUTICALLY ACTIVE URIDINE ESTERS

(75) Inventor: Rudy Susilo, Köln (DE)

(73) Assignee: Trommsdorff GmbH & Co. KG Arzneimittel, Alsdorf (DE)

( * ) Notice: Subject to any disclaimer, the term of this patent is extended or adjusted under 35 U.S.C. 154(b) by 135 days.

(21) Appl. No.: 10/951,764

(22) Filed: Sep. 29, 2004

(65) Prior Publication Data

US 2005/0043269 A1   Feb. 24, 2005

Related U.S. Application Data

(62) Division of application No. 10/476,287, filed as application No. PCT/EP02/04725 on Apr. 29, 2002.

(60) Provisional application No. 60/330,429, filed on Oct. 22, 2001, provisional application No. 60/288,090, filed on May 3, 2001.

(30) Foreign Application Priority Data

Apr. 30, 2001   (EP) ................................. 01110608
Oct. 18, 2001   (EP) ................................. 01124879

(51) Int. Cl.
*A61K 31/7072* (2006.01)
*A61K 31/70* (2006.01)
*C07H 19/00* (2006.01)

(52) U.S. Cl. ................. 514/50; 514/49; 536/28.53

(58) Field of Classification Search ............... 514/50, 514/28.53, 49; 536/28.53
See application file for complete search history.

(56) References Cited

U.S. PATENT DOCUMENTS 5,583,117 A * 12/1996 von Borstel et al. ........... 514/50
5,736,531 A    4/1998 von Borstel et al.

OTHER PUBLICATIONS

Gura (Science, 1997, 278(5340):1041-1042).*
Jain (Sci. Am., 1994, 271:58-65).*
Curti (Crit. Rev. in Oncology/Hematology, 1993, 14:29-39).*
J. Huang et al, Synthetic Communications, vol. 27, 1997, pp. 681-690.
P. Moris et al, J. Org. Chem, vol. 58, 1993, pp. 653-660.
Piera T. Calissi et al.; The Annals of Pharmacotherapy; vol. 29, Jul./Aug. 1995, pp. 769-777.

* cited by examiner

*Primary Examiner*—Shaojia Anna Jiang
*Assistant Examiner*—Michael C. Henry
(74) *Attorney, Agent, or Firm*—Birch, Stewart, Kolasch & Birch, LLP

(57) ABSTRACT

The present invention relates to novel uridine esters of the general formula

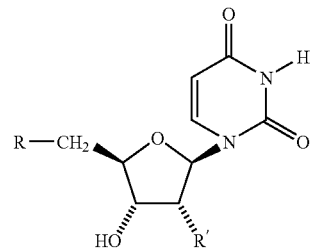

wherein
R represents a carboxylic acid residue, preferably a fatty acid residue and R' represents hydrogen or a hydroxy group, their use as pharmaceutically active agents against a variety of diseases, methods for the preparation of said uridine esters and pharmaceutical compositions containing at least one uridine ester as active ingredient. The present invention relates also to a drug combination comprising free fatty acids and/or fatty acid esters and uridine, deoxyuridine, uridine monophosphate and/or deoxyuridine monophosphate, and to the use of such a drug combination.

7 Claims, 7 Drawing Sheets

Linoleic acid

Pristanic acid

Phytanic acid

Eicosapentaenoic acid

β-Retinoic acid   (all-trans isomer)

Lipoic acid

Dihydrolipoic acid

Tariric acid

6,9-Octadecenynoic acid

Crepenynic acid

Heisteric acid

H$_3$C—(CH$_2$)$_{21}$—CH(OH)—COOH

Cerebronicic acid

H$_3$C—(CH$_2$)$_7$—CH=CH—(CH$_2$)$_{12}$—CH(OH)—COOH

Nervonic acid

H$_3$C—(CH$_2$)$_5$—CH(OH)—CH$_2$—CH=CH—(CH$_2$)$_7$—COOH

Ricinoleic acid

γ-Linolenic acid

α-Linolenic acid

EPA

DHA

β-D-Ribose

β-D-2-Deoxyribose

Uracil

Cytosine

Thymine

PHARMACEUTICALLY ACTIVE URIDINE ESTERS

This application is a Divisional of co-pending application Ser. No. 10/476,287 filed on Oct. 29, 2003 and for which priority is claimed under 35 U.S.C. § 120. Application Ser. No. 10/476,287 is the national phase of PCT International Application No. PCT/EP02/04725 filed on Apr. 29, 2002 under 35 U.S.C. § 371. The entire contents of each of the above-identified applications are hereby incorporated by reference. This application also claims priority of Application No. 011 10 608.5 filed in Europe on Apr. 30, 2001, Provisional application Ser. No. 60/288,090 filed in the United States on May 3, 2001, application Ser. No. 011 24 879.6 filed in Europe on Oct. 18, 2001, and Provisional Application No. 60/330,429 filed in the United States on Oct. 22, 2001 under 35 U.S.C. § 119.

The present invention relates to novel uridine esters, their use as pharmaceutically active agents against a variety of diseases, methods for the preparation of said uridine esters and pharmaceutical compositions containing at least one uridine ester as active ingredient. The present invention relates also to a drug combination comprising free fatty acids and/or fatty acid esters and uridine, deoxyuridine, uridine monophosphate and/or deoxyuridine monophosphate, and to the use of such a drug combination.

BACKGROUND OF THE INVENTION

Fatty Acids:

Carboxylic acids occur in many molecular forms. At first it must be recalled that if the majority of the fatty acids found in lipids are monocarboxylic acids, some of the fatty acids are dicarboxylic and constitute important metabolic products of the previous ones.

To describe precisely the structure of a fatty acid molecule, one must give the length of the carbon chain (number of carbon atoms), the number of double bonds and also the exact position of these double bonds. This will define the biological reactivity of the fatty acid molecule.

Most fatty acids are straight-chain compounds with in most cases an even number of carbon atoms. Chain-lengths range from 2 to 80 carbon atoms, but commonly from 12 up to 24. With a chain length from 2 to 4 carbon atoms they are called short-chain, from 6 to 10 they are called medium-chain and 12 up to 24 they are called long-chain fatty acids. Their physical and biological properties are related to this partition in 3 classes.

Fatty acids can be further subdivided into well-defined families according to their structure:

a) Saturated fatty acids
b) Monoenoic fatty acids
c) Polyenoic fatty acids
   methylene interrupted
     polymethylene interrupted
       conjugated
       isolated
d) Mono- and multibranched fatty acids
e) Ring containing fatty acids
   cyclopropane acids
   furanoid acids
   epoxy acids
   lipoic acid
f) Acetylenic fatty acids
g) Hydroxy fatty acids
h) Sulfur containing fatty acids
i) Dicarboxylic acids
j) Fatty acid amides
k) Keto fatty acids.

The simplest fatty acids are referred to as saturated fatty acids. They have no unsaturated linkages and cannot be altered by hydrogenation or halogenation. When double bonds are present, fatty acids are said unsaturated, monounsaturated (MUFA) if only one double bond is present and polyunsaturated (PUFA) if they have two or more double bonds generally separated by a single methylene group (methylene-interrupted unsaturation).

To describe these unsaturated fatty acids, two ways are offered:

The Chemist's Terminology:

The carbon atoms are counted from the carboxyl group which put the emphasis on the double bond closest to this group. As an example: 18:2 Δ9,12-octadecadienoic acid or cis-9, cis-12-octadecadienoic acid, the trivial name: linoleic acid. The double bonds have usually a Z (cis) configuration but can have also a E (trans) configuration.

The Biochemist's and Physiologist's Terminology: The double bonds are counted from the methyl group determining the metabolic family, noted by n-x (n being the total number of carbon atoms, x the position of the last double bond). The other double bonds are deduced from the first one by adding 3 (this is the most frequent structure, non-conjugated fatty acids, but sometimes by adding 2, these double bonds are said conjugated).

Thus linoleic acid (cf. FIG. 1a) or cis-9, cis-12-octadecadienoic acid is also named in the shorthand nomenclature 18:2 (n-6). This compound has 18 carbon atoms, 2 double bonds and 6 carbon atoms from the last double bond to the terminal methyl group. In the old literature it was designated 18:2ω6. 18−6=12, 12−3=9 hence D9, 12.

Saturated fatty acids have commonly straight chains and even carbon number (n=4–30). They have the general formula: $CH_3(CH_2)_nCOOH$. Table 1 summarizes some saturated acids and their corresponding trivial names.

TABLE 1

Most common saturated fatty acids

| Systematic name | Trivial name | Shorthand designation |
|---|---|---|
| Butanoic acid | Butyric acid | 4:0 |
| Hexanoic~ | Caproic~ | 6:0 |
| Octanoic~ | Caprylic~ | 8:0 |
| Decanoic~ | Capric~ | 10:0 |
| Dodecanoic~ | Lauric~ | 12:0 |
| Tetradecanoic~ | Myristic~ | 14:0 |
| Hexadecanoic~ | Palmitic~ | 16:0 |
| Heptadecanoic~ | Margaric~ | 17:0 |
| Octadecanoic~ | Stearic~ | 18:0 |
| Eicosanoic~ | Arachidic~ | 20:0 |
| Docosanoic~ | Behenic~ | 22:0 |
| Tetracosanoic~ | Lignoceric~ | 24:0 |

Monoenoic fatty acids are monounsaturated normal fatty acids which are widespread in the living world where they occur mostly as their cis-isomers. They have the general structure $CH_3(CH_2)_xCH=CH(CH_2)_yCOOH$. They can have the unique double bond in a number of different positions, but the most common are of the n-9 series, as oleic acid from olive oil (cis-9-octadecenoic acid) and from quite all seed oils. Some important monoenoic acids are listed below:

TABLE 2

Monoenoic fatty acids

| Systematic name | Trivial name | Shorthand designation |
| --- | --- | --- |
| cis-9-tetradecenoic acid | Myristoleic acid | 14:1(n-5) |
| cis-9-hexadecenoic~ | Palmitoleic~ | 16:1(n-7) |
| cis-6-octadecenoic~ | Petroselinic~ | 18:1(n-12) |
| cis-9-octadecenoic~ | Oleic~ | 18:1(n-9) |
| cis-11-octadecenoic~ | Vaccenic~ | 18:1(n-7) |
| cis-9-eicosenoic~ | Gadoleic~ | 20:1(n-11) |
| cis-11-eicosenoic~ | Gondoic~ | 20:1(n-9) |
| cis-13-docosenoic~ | Erucic~ | 22:1(n-9) |
| cis-15-tetracosenoic~ | Nervonic~ | 24:1(n-9) |

Oleic acid is probably the most common fatty acid (60-70% in olive oil). Several positional isomers of oleic acid exist with the cis double bond in the (n-12) or (n-7) position but trans-isomers are known: Elaidic acid (t9-octadecenoic acid) and t-vaccenic acid (t11-octadecenoic acid) are found in the rumen and in lipids of ruminant animals.

An unusual trans fatty acid, t3-hexadecenoic acid (trans-16:1 n-13), occurs in eukaryotic photosynthetic membranes from higher plants and green algae.

Polyenoic fatty acids are also called polyunsaturated fatty acis (PUFA). These fatty acids have 2 or more cis double bonds which are most frequently separated from each other by a single methylene group (methylene-interrupted polyenes). Linoleic acid is a typical member of this group. Some other polyunsaturated fatty acids undergo a migration of one of their double bonds which are not again methylene-interrupted and are known as conjugated fatty acids. Some unusual fatty acids do have not the regular structure with a methylene group between two double bonds, but are polymethylene-interrupted polyenes. They are found in certain classes of plants, marine invertebrates and insects. Brominated long-chain fatty acids have been isolated from phospholipids of primitive marine animals such as sponges.

The most important polyenoic fatty acids can be grouped into 2 series with a common structural feature: $CH_3(CH_2)_xCH=CH-$ with x=4 for the (n-6) series and with x=1 for the (n-3) series. Eicosapentaenoic acid is a common polyene of the (n-3) series having the double bonds in the 5, 8, 11, 14, and 17 positions. Table 3 summarizes the most common polyenoic fatty acids.

TABLE 3

The most common polyenoic fatty acids are listed below:

| Systematic name | Trivial name | Shorthand designation |
| --- | --- | --- |
| 9,12-octadecadienoic acid | Linoleic acid | 18:2(n-6) |
| 6,9,12-octadecatrienoic~ | γ-Linolenic~ | 18:3(n-6) |
| 8,11,14-eicosatrienoic~ | Dihomo-γ-linolenic~ | 20:3(n-6) |
| 5,8,11,14-eicosatetraenoic~ | Arachidonic~ | 20:4(n-6) |
| 7,10,13,16-docosatetraenoic~ | — | 22:4(n-6) |
| 4,7,10,13,16-docosapentaenoic~ | — | 22:5(n-6) |
| 9,12,15-octadecatrienoic~ | α-Linolenic~ | 18:3(n-3) |
| 6,9,12,15-octadecatetraenoic~ | Stearidonic~ | 18:4(n-3) |
| 8,11,14,17-eicosatetraenoic~ | — | 20:4(n-3) |
| 5,8,11,14,17-eicosapentaenoic~ | EPA | 20:5(n-3) |
| 7,10,13,16,19-docosapentaenoic~ | DPA | 22:5(n-3) |
| 4,7,10,13,16,19-docosahexaenoic~ | DHA | 22:6(n-3) |
| 5,8,11-eicosatrienoic~ | Mead acid | 20:3(n-9) |

The most common polyene acids are octadecatrienoic acids (7 species are known). Eleostearic acid (9c11t13t) is found in tong oil and had an industrial importance, calendic acid (8t10t12c) is found in *Calendula officinalis* and catalpic acid (9c11t13c) is found in *Catalpa ovata*.

Recently, novel polyene fatty acids with different chain lengths and varying unsaturation were described: 16:5, 18:4, 20:5, 20:6, and unexpectedly 22:7. All these species have in common 4 conjugated all-cis double bonds as in 18:4 with their position in 6, 8, 10, and 12, the novel conjugated docosaheptadecanoic acid having its double bonds in 4, 7, 9, 11, 13, 16, and 19, it was named stellaheptaenoic acid.

Among the unsaturated polymethylene-interrupted fatty acids found in the plant kingdom those with a cis-5 ethylenic bond are present in various sources. The three most frequent fatty acids with that structure are taxoleic acid (all-cis-5,9-18:2), pinolenic acid (all-cis-5,9,12-18:3) which is found in seeds of conifers, *Teucrium* and also in tall oil, and sciadonic acid (all-cis-5,11,14-20:3). These fatty acids are present in seed oil at levels from about 1% up to 25%. Similar species with 4 double bonds are also described.

Some isoprenoid fatty acids are known. In this group, the most interesting is retinoic acid (cf. FIG. 1a) which derives from retinol and has important functions in cell regulation.

Mono- and multibranched fatty acids, preferably monomethyl branched fatty acids are found in animal and microbial lipids, e.g. mycobacteria. As for hydrocarbons, they have generally either an iso- or an anteiso-structure. For instance, 14-methyl pentadecanoic acid (isopalmitic acid) is of the iso-series and 13-methyl pentadecanoic acid is of the corresponding anteiso-series. Further examples for branched fatty acids are pristanic acid and phytanic acid as shown in FIG. 1a.

Some fatty acids contain either in the chain a cyclopropane ring (present in bacterial lipids) or a cyclopropene ring (present in some seed oils), or at the end of the chain a cyclopentene ring (seed oils). Among cyclopropane acids, lactobacillic acid (11,12-methyleneoctadecanoic acid) is found mainly in gram-negative bacteriae. Another cyclopropane fatty acid (9,10-methylenehexadecanoic acid) was recently shown to be present in phospholipids of heart and liver mitochondria.

Cyclopropene acids are found in Malvales seed oils, and Baobab, Kapok and Mowrah seed oils. Among cyclopentenyl acids, Chaulmoogric acid is found in chaulmoogra oil from seeds of *Flacourtiaceae* (*Hydnocarpus*), which was used in folk medicine for treatment of leprosy.

Epoxy acids are present in a number of seed oils. The natural species are all C18 compounds, saturated on unsaturated. For example, 9,10-epoxystearic and 9,10-epoxyoctadec-12-enoic (coronaric acid) acids are found in sunflower seeds (*Chrysanthemum*).

Lipoic acid (cf. FIG. 1b) was first considered as a microbial growth factor but it was found not only in yeast but also in beef liver from which it was first isolated in pure form. Lipoic acid was named also thioctic acid or 1,2-dithiolane-3-pentanoic acid. After its absorption, this acid is reduced enzymatically by NADH or NADPH to dihydrolipoic acid (or 6,8-dithiane octanoic acid) in various tissues.

First shown necessary for bacteria, lipoic acid was demonstrated to be a coenzyme in the glycine cleavage system and in the dehydrogenase complex. Now, lipoic acid is considered as an efficient antioxidant since with its reduced form it constitutes a redox couple via modulation of NADH/NAD ratio. Consequently, lipoic acid has gained a special interest as a therapeutic agent. It can scavenge hydroxyl and peroxyl radicals but also chelates transition metals. It is also considered that lipoic acid is perhaps the most powerful of all the antioxidants, it may offer an efficient protection against many heart diseases, it is currently used to relieve the complications of diabetes.

Acetylenic fatty acids, also known as ethynoic acids, include fatty acids which contain a triple bond and eventually one or two double bonds. For instance, tariric acid (6-octadecynoic acid) was found in tariri seeds from *Picramnia sow*, a plant indigenous to Guatemala. Table 4 shows further examples of acetylenic fatty acids.

TABLE 4

Acetylenic fatty acids

| Systematic name | Trivial name |
|---|---|
| 6-octadecynoic acid | Tariric acid |
| t11-octadecen-9-ynoic~ | Santalbic or Ximenynic~ |
| 9-octadecynoic~ | Stearolic~ |
| 6-octadecen-9-ynoic~ | 6,9-octadecenynoic~ |
| t10-heptadecen-8-ynoic~ | Pyrulic~ |
| 9-octadecen-12-ynoic~ | Crepenynic~ |
| t7,t11-octadecadiene-9-ynoic~ | Heisteric~ |
| t8,t10-octadecadiene-12-ynoic~ | — |
| 5,8,11,14-eicosatetraynoic~ | ETYA |

In hydroxy fatty acids the hydroxyl group may occur at various positions in the carbon chain which can be saturated or monoenoic. Some polyhydroxy fatty acids are known, which are most frequently produced by lipoxygenase activities. 2-Hydroxy acids (or α-hydroxy acids) are found in plants (chain from 12 up to 24 carbon atoms) and in animal wool waxes, skin lipids and specialized tissues, mainly in brain. 2-Hydroxytetracosanoic acid (cerebronic acid) and 2-hydroxy-15-tetracosenoic acid (hydroxynervonic acid) are constituents of the ceramide part of cerebrosides and 3-hydroxy acids (or β-hydroxy acids) occur in some bacterial lipids. Further examples are ricinoleic acid (12-hydroxy-9-octadecenoic acid) which characterizes castor bean oil and lesquerolic acid, the C20 homologue of ricinoleic acid (14-hydroxy-11-eicosenoic acid).

Although the dicarboxylic acids do not occur in appreciable amounts as components of animal or vegetal lipids, they are in general important metabolic products of fatty acids since they originate from them by oxidation. They have the general type formula: $HOOC-(CH_2)_n-COOH$. Short-chain dicarboxylic acids are of great importance in the general metabolism and up to n=3 they cannot be considered as lipids since their water solubility is important. The simplest of these intermediates is oxalic acid (n=0), the others are malonic (n=1), succinic (n=2) and glutaric (n=3) acids. The other lipid members of the group found in natural products or from synthesis have a "n" value from 4 up to 21. Examples thereof are: adipic acid (n=4), pimelic acid (n=5), suberic acid (n=6), azelaic acid (n=7), sebacic acid (n=8), brassylic acid (n=11), and thapsic acid (n=14).

Ribose and Deoxyribose:

Ribose and deoxyribose are pentoses. Ribose is also called ribofuranose because of the structural relationship to furane. The only structural difference between ribose and deoxyribose is the loss of an hydroxy group in position 2'C of the heterocyclic ring. FIG. 2 shows the structures of ribose and deoxyribose.

Nucleosides and Nucleotides:

These are compounds in which a purine or pyrimidine base is covalently bound to a sugar. If the base is bound to ribose the result is a ribonucleoside (base+sugar=nucleoside), and if bound to deoxyribose then the nucleoside is deoxyribonucleoside. In deoxyribose the OH-group on 2'C is replaced with hydrogen so becomes deoxy.

The bonding between the base and the sugar involves 1'C OH-group of the sugar, and the N9 nitrogen of a purine or N1 of a pyrimidine in an N-beta-glycosidic linkage. The nucleosides containing deoxyribose possess the same type of glycosidic linkage.

FIG. 2 shows the three purine bases uracil, cytosine, and thymine.

TABLE 5

Nomenclature

| Base | Ribonucleoside | Ribonucleotide-5-monophosphate |
|---|---|---|
| Adenine | Adenosine (A) | AMP |
| Guanine | Guanosine (G) | GMP |
| Uracil | Uridine (U) | UMP |
| Cytosine | Cytidine (C) | CMP |
| Thymine | Thymidine (T) | TMP |

| Base | DeoxyRibonucleoside | DeoxyRibonucleotide-5-monophosphate |
|---|---|---|
| Adenine | Deoxyadenosine (dA) | dAMP |
| Guanine | Deoxyguanosine (dG) | dGMP |
| Uracil | Deoxyuridine (dU) | dUMP |
| Cytosine | Deoxycytidine (dC) | dCMP |
| Thymine | Deoxythymidine (dT) | dTMP |

In order to distinguish the numbering of the sugar ring and numbering of the bases the sugar numbers are primed, e.g. 3'5'. Thus, 5' refers to 5'C of the sugar ring.

These are phosphate esters of the nucleosides and they are fairly strong acids. The phosphoric acid is always esterified to the sugar group (base+sugar+phosphate=nucleotide). The phosphoric acid could be located on the 2', 3' or 5'C of the sugar residue. However natural ribonucleotides and deoxyribonucleotides have the phosphoric acid on the 5'C position.

The phosphoric acid can undergo further phosphorylation to produce diphosphates and triphosphates, e.g. ADP and ATP. So for each nucleotide monophosphate there is also a nucleotide diphosphate and a nucleotide triphosphate. The di and tri nucleotides do not occur in DNA or RNA only the monophosphate nucleotides. The di and triphosphate nucleotides do occur naturally, and play very important roles in many aspects of biochemical metabolism.

Object of the present invention is to provide novel compounds and novel drug combinations which can be used for prophylaxis and/or treatment of a variety of diseases and disorders comprising diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, *Chlamydia pneumoniae*, and retroviral infections (HIV, AIDS), together with methods for said treatment and pharmaceutical compositions used within said methods.

This object is solved by the disclosure of the independent claims. Further advantageous features, aspects and details of the invention are evident from the dependent claims, the description, the examples and the figures of the present application.

DESCRIPTION OF THE INVENTION

The present invention relates to compounds having the general formula (I):

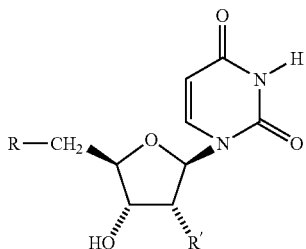

wherein

R represents R"—COO;

R' represents hydrogen or a hydroxy group;

R" represents a alkyl chain with 8 to 30 carbon atoms, a monobranched or multibranched alkyl chain with 8 to 30 carbon atoms, a monoenoic alkyl chain with 8 to 30 carbon atoms, a monoenoic branched alkyl chain with 8 to 30 carbon atoms, a polyenoic alkyl chain with 8 to 30 carbon atoms, a polyenoic branched alkyl chain with 8 to 30 carbon atoms, a branched or unbranched alkyl chain with 8 to 30 carbon atoms containing a carbocyclic or heterocyclic ring, a monoynoic alkyl chain with 8 to 30 carbon atoms, a monoynoic branched alkyl chain with 8 to 30 carbon atoms, a polyynoic alkyl chain with 8 to 30 carbon atoms, a polyynoic branched alkyl chain with 8 to 30 carbon atoms, a alkyl chain with 8 to 30 carbon atoms containing at least one double and one triple bond, a branched alkyl chain with 8 to 30 carbon atoms containing at least one double and one triple bond, a hydroxy group or thiol group containing branched or unbranched and/or saturated or unsaturated alkyl chain with 8 to 30 carbon atoms, and pharmaceutically acceptable salts thereof.

The compounds of the general formula (I) and/or pharmaceutically acceptable salts thereof exhibit excellent activity against a variety of diseases and disorders and therefore are useful as pharmaceutically active agents.

The compounds according to formula (I) can be synthesized starting from hydroxy group protected nucleosides or deoxynucleosides. As protecting groups for the two nucleoside hydroxy groups in position 3 and 4, normally acetals and preferably ketals are used. As protecting groups for the deoxynucleoside hydroxy group in position 3, preferably acid sensitive OH-protecting groups for secondary alcohols are used. These OH-protected nucleosides or deoxynucleosides are used as starting material and are reacted with carboxylic acid, carboxylic acid halogenid, carboxylic acid cyanide, carboxylic acid azide, and/or carboxylic acid anhydride. In the case of a non-activated carboxylic acid is used, reagents such as dicyclohexylcarbodiimide (DCC) are needed in order to support ester formation.

In the case, a carboxylic acid chloride, bromide, cyanide, or azide is used, a base preferably an organic base such as pyridine, dimethyl aminopyridine (DMAP), triethylamine, imidazole ect. may be added to the reaction mixture.

Normally equimolar amounts of (deoxy)nucleoside and carboxylic acid or carboxylic acid derivatives (carboxylic acid halogenids, -cyanides, -azides, -anhydrides) are used within the process, but also a high excess of one reactant can be used. Preferred solvents comprise polar aprotic solvents such as dichloromethane, chloroform, DMF, or ethers (THF, dioxane, diethylether, TBDME, etc.).

In the last step of the process the OH-protecting group is removed preferably under smooth acidic conditions optionally at elevated temperatures between 80 and 100° C. Solvents such as acetic acid or a mixture of water and acetic acid or alcohols such as methanol or ethanol gave good results. A broad variety of organic acids such as benzene sulfonic acids, citric acid, methane sulfonic acid, oxalic acid, etc. may be used in catalytic amounts for ketal and acetal cleavage.

Furthermore, it has turned out to be advantageous to carry out all reaction steps under exclusion of light. Purification of the products were performed according to standard procedures well known in the state of the art.

The compounds of the invention are basic and form pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, d-o-tolyltartaric acid, tartronic acid, α-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

The inventive compounds of the general formula (I) exhibit also acidic properties, because of the uracil moiety and in addition thereto, depending upon the reagents used for the ester formation, e.g. in the event a dicarboxylic acid is used for ester formation, further acidic groups are present and the inventive compounds are able to form salts with organic or inorganic bases, too. Thus, for example, if there are carboxylic acid substituents in the molecule, salts may be formed with inorganic as well as organic bases such as, for example, NaOH, KOH, NH$_4$OH, tetraalkylammonium hydroxide, and the like.

Thus, suitable pharmaceutically acceptable salts of the compounds of the present invention include addition salts formed with organic or inorganic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose. Examples include alkali or alkaline-earth hydroxides, alkali or alkaline-earth alkoxides, alkali or alkaline-earth carbonates or bicarbonates, and/or organic bases such as, i.a., ammonia, primary, secondary and tertiary amines, such as, e.g., ethanolamine, glucamine, N-methyl- and N,N-dimethylglucamine, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, morpholine, 1-adamantylamine, benzathine, or salts derived from amino acids like arginine, lysine, ornithine or amides of originally neutral or acidic amino acids. The physiologically acceptable salts such as the sodium or potassium salts and the amino acid salts can be used medicinally as described below and are preferred.

The compounds of the present invention and/or their pharmaceutically acceptable salts are useful for prophylaxis and/or treatment of diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, *Chlamydia pneumoniae*, depression, obesity, stroke, pain, asthma and retroviral infections (HIV, AIDS), including opportunistic infections.

Furthermore, the compounds of the general formula (I) and/or pharmaceutically acceptable salts thereof can be used for the manufacture of a pharmaceutical formulation useful as stimulant drug and/or for prophylaxis and/or treatment of diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, *Chlamydia pneumoniae*, depression, obesity, stroke, pain, and retroviral infections (HIV, AIDS), including opportunistic infections.

Furthermore, the inventive compounds are useful as stimulant drugs or stimulants. As used herein, the term "stimulant drug" or "stimulant" refers to pharmaceutically active compounds that temporarily increases the rate of body functions. The principle pharmacological effect of stimulant drugs is to stimulate the central nervous system and peripheral system of the body. Some stimulants affect only a specific organ such as the heart, lungs, brain, or nervous system. Stimulants comprise substances such as amineptine, amiphenazole, amphetamines, bromantan, caffeine, carphedon, cocaine, ephedrines, fencamfamine, mesocarb, pentylentetrazol, pipradol, salbutamol, salmeterol, terbutaline, and related substances. Stimulants which effect the central nervous system comprise methcathione, tenamfetamine, MDMA, amfetamine, metamfetamine, fenetylline, methylphenidate, phenmetrazine, amfepramone, mesocarb, pemoline, phentermine, and the like.

Amphetamine-type stimulants can be used for the treatment of attention-deficit disorder, narcolepsy, and of obesity. Beside that use of stimulants the main therapeutic applications of these psychoactive stimulant drugs are anxiety, depression, epilepsy, psychosis and sleeping disorders.

As used herein the term "stimulate the organism" refers to the effect of the inventive compounds according to formula (I) on specific organs and especially on the central nervous system resulting in a similar therapeutic effect as obtained by the use of a stimulant of the state of the art as mentioned above. Thus, the inventive compounds can be used to treat attention-deficit disorder, narcolepsy, obesity, anxiety, depression, epilepsy, psychosis preventation and reversal of fatigue, asthma and sleeping disorders and can replace a common stimulant.

The inventive uridine and deoxyuridine compounds of the general formula (I) comprise a carboxylic acid esters derived from the corresponding fatty acid on position 5'C of the ribose or deoxyribose moiety. The alkyl chain of said fatty acid comprises 8 to 30 carbon atoms. Preferred are these alkyl chains with 8 or 10 to 24 carbon atoms, more preferably 14 to 22 carbon atoms, even more preferably 18 to 22 carbon atoms, and most preferably 18, 20, or 22 carbon atoms.

Thus, preferred are these inventive compounds wherein R" represents an alkyl chain with 8 to 24 carbon atoms, a monobranched or multibranched alkyl chain with 8 to 24 carbon atoms, a monoenoic alkyl chain with 8 to 24 carbon atoms, a monoenoic branched alkyl chain with 8 to 24 carbon atoms, a polyenoic alkyl chain with 8 to 24 carbon atoms, a polyenoic branched alkyl chain with 8 to 24 carbon atoms, a branched or unbranched alkyl chain with 8 to 24 carbon atoms containing a carbocyclic or heterocyclic ring, a monoynoic alkyl chain with 8 to 24 carbon atoms, a monoynoic branched alkyl chain with 8 to 24 carbon atoms, a polyynoic alkyl chain with 8 to 24 carbon atoms, a polyynoic branched alkyl chain with 8 to 24 carbon atoms, a hydroxy group or thiol group containing branched or unbranched and/or saturated or unsaturated alkyl chain with 8 to 24 carbon atoms and even more preferred are compounds wherein R" represents a monoenoic alkyl chain with 10 to 24 carbon atoms, a monoenoic branched alkyl chain with 10 to 24 carbon atoms, a polyenoic alkyl chain with 10 to 24 carbon atoms, a polyenoic branched alkyl chain with 10 to 24 carbon atoms, a branched or unbranched alkyl chain with 8 to 20 carbon atoms containing a carbocyclic or heterocyclic ring, a monoynoic alkyl chain with 10 to 24 carbon atoms, a monoynoic branched alkyl chain with 10 to 24 carbon atoms, a polyynoic alkyl chain with 10 to 24 carbon atoms, a polyynoic branched alkyl chain with 10 to 24 carbon atoms.

Also preferred are carbon chains with an even number of carbon atoms.

Suitable fatty acids which can be used for the formation of carboxylic esters are disclosed in section Fatty acids of the description, especially in tables 1, 2, 3, and 4 of the present application.

Long chain carboxylic acids as listed in Table 1, branched or multibranched carboxylic acids like isopalmitic acid, pristanic acid or phytanic acid, and monoenoic acids as summarized in Table 2 may be used for the synthesis is the inventive compounds of the general formula (I). Preferred is the use of acetylenic acids as shown in Table 4 and hydroxy group bearing acids like cerebronic acid, hydroxynervonic acid, ricinoleic acid, and lesquerolic acid. More preferred are unsaturated carboxylic acids. Examples for the most common unsaturated carboxylic acids are given in Table 3 of the description. Further examples are eleostearic acid, catalpic acid, calendic acid, docosaheptadecanoic acid, taxoleic acid, pinolenic acid, sciadonic acid, and retinoic acid.

Also preferred are carboxylic acids comprising carbocyclic or heterocyclic ring. Examples for ring containing carboxylic acids are 11,12-methyleneoctadecanoic acid, 9,10-methylenehexadecanoic acid, coronaric acid, also known as thioctic acid or its reduced form, the dihydrolipoic acid also known as 6,8-dithiane octanoic acid.

Among the unsaturated and ring containing carboxylic acids more preferred are linoleic acid, γ-linolenic acid, dihomo-γ-linolenic acid, arachidonic acid, 7,10,13,16-docosatetraenoic acid, 4,7,10,13,16-docosapentaenoic acid, α-linolenic acid, stearidonic acid, 8,11,14,17-eicosatetraenoic acid, EPA, DPA, DHA, Mead acid, (R,S)-lipoic acid, (S)-lipoic acid, (R)-lipoic acid, eleostearic acid, catalpic acid, calendic acid, docosaheptadecanoic acid, taxoleic acid, pinolenic acid, sciadonic acid, and retinoic acid.

Most preferred are the following carboxylic acids: γ-linolenic, α-linolenic, EPA, DHA, (R,S)-lipoic acid, (S)-lipoic acid, and (R)-lipoic acid.

Thus, compounds of the present invention are preferred wherein R" represents dodecanyl, hexadecanyl, octadecanyl, eicosanyl, docosanyl, tetracosanyl, cis-9-tetradecenyl cis-9-hexadecenyl, cis-6-octadecenyl, cis-9-octadecenyl. cis-11-octadecenyl, cis-9-eicosenyl, cis-11-eicosenyl, cis-13-docosenyl, cis-15-tetracosenyl, 9,12-octadecadienyl, 6,9,12-octadecatrienyl, 8,11,14-eicosatrienyl, 5,8,11,14-eicosatetraenyl, 7,10,13,16-docosatetraenyl, 4,7,10,13,16-docosapentaenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 1,2-dithiolane-3-pentanyl, 6,8-dithiane octanyl, docosaheptadecanyl, eleostearyl, calendyl, catalpyl, taxoleyl, pinolenyl, sciadonyl, retinyl, 14-methyl pentadecanyl, pristanyl, phytanyl, 11,12-methyleneoctadecanyl, 9,10-methylenehexadecanyl, 9,10-epoxystearyl, 9,10-epoxyoctadec-12-enyl, 6-octadecynyl, t11-octadecen-9-ynyl, 9-octadecynyl, 6-octadecen-9-ynyl, t10-heptadecen-8-ynyl, 9-octadecen-12-ynyl, t7,t11-octadecadiene-9-ynyl, t8,t10-octadecadiene-12-ynyl, 5,8,11,14-eicosatetraynyl, 2-hydroxytetracosanyl, 2-hydroxy-15-tetracosenyl, 12-hydroxy-9-octadecenyl, and 14-hydroxy-11-eicosenyl.

More preferred are these inventive compounds wherein R" represents 9,12-octadecadienyl, 6,9,12-octadecatrienyl, 8,11,14-eicosatrienyl, 5,8,11,14-eicosatetraenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 1,2-dithiolane-3-pentanyl, and 6,8-dithiane octanyl.

Most preferred are the following compounds of the general formula (I):
Compound 1: (2'R,3'S,4'R,5'R)-Octadeca-6,9,12-trienoic acid 5'-(2,4-dioxo-3,4-dihydro-2H-pyrimidine-1-yl)-3',4'-dihydroxy-tetrahydrofuran-2'-ylmethyl ester,
Compound 2: (2'R,3'S,4'R,5'R)-Octadeca-9,12,15-trienoic acid 5'-(2,4-dioxo-3,4-dihydro-2H-pyrimidine-1-yl)-3',4'-dihydroxy-tetrahydrofuran-2'-ylmethyl ester,
Compound 3: (2'R,3'S,4'R,5'R)-Icosa-5,8,11,14,17-pentaenoic acid 5'-(2,4-dioxo-3,4-dihydro-2H-pyrimidine-1-yl)-3',4'-dihydroxy-tetrahydrofuran-2'-ylmethyl ester,
Compound 4: (2'R,3'S,4'R,5'R)-Docosa-4,7,10,13,16,19-hexaenoic acid 5'-(2,4-dioxo-3,4-dihydro-2H-pyrimidine-1-yl)-3',4'-dihydroxy-tetrahydrofuran-2'-ylmethyl ester,
Compound 5: (2'R,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester,
Compound S5: (2'R,3S,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester,
Compound R5: (2'R,3R,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester,
Compound 5': (2'R,3'S,4'R,5'R)-6,8-Dimercapto-octanoic acid 5'-(2,4-dioxo-3,4-dihydro-2H-pyrimidine-1-yl)-3',4'-dihydroxy-tetrahydrofuran-2'-ylmethyl ester, and pharmaceutically acceptable salts of these compounds.

The inventive compounds of the general formula (I) and/or pharmaceutically acceptable salts thereof are administered in a dosage corresponding to an effective concentration in the range of 1-10000 mg, preferably in the range of 1-5000 mg, more preferably in the range of 10-1000 mg, and most preferably in the range of 100-800 mg.

Another preferred embodiment of the present invention relates to the combination of at least one compound of the general formula (I) and/or pharmaceutically acceptable salts thereof with further therapeutic drugs, agents, or compounds. Said further therapeutic compounds are selected from the group comprising vitamins and anti-retroviral drugs. Suitable vitamins are vitamin A, B1, B2, B6, B12, C, E, and pharmaceutically acceptable salts thereof.

A further aspect of the present invention relates to a method for preventing and/or treating diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, *Chlamydia pneumoniae*, depression, obesity, stroke, pain, and retroviral infections (HIV, AIDS), including opportunistic infections, in a mammal, including a human, which comprises administering to said mammal an amount of at least one compound of the general formula (I) and/or pharmaceutically acceptable salts thereof effective to treat the disease. Also disclosed is a method for stimulating the organism, especially specific organs and/or the central nervous system of a mammal, especially a human, comprising the step of administering to said mammal an amount of at least one inventive compounds and/or a salt thereof effective to stimulate body functions of said mammal.

Preferably inventive uridine or deoxyuridine compounds are used within said method wherein R" represents dodecanyl, hexadecanyl, octadecanyl, eicosanyl, docosanyl, tetracosanyl, cis-9-tetradecenyl, cis-9-hexadecenyl, cis-6-octadecenyl, cis-9-octadecenyl, cis-11-octadecenyl, cis-9-eicosenyl, cis-11-eicosenyl, cis-13-docosenyl, cis-15-tetracosenyl, 9,12-octadecadienyl, 6,9,12-octadecatrienyl, 8,11,14-eicosatrienyl, 5,8,11,14-eicosatetraenyl, 7,10,13,16-docosatetraenyl, 4,7,10,13,16-docosapentaenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 1,2-dithiolane-3-pentanyl, 6,8-dithiane octanyl, docosaheptadecanyl, eleostearyl, calendyl, catalpyl, taxoleyl, pinolenyl, sciadonyl, retinyl, 14-methyl pentadecanyl, pristanyl, phytanyl, 11,12-methyleneoctadecanyl, 9,10-methylenehexadecanyl, 9,10-epoxystearyl, 9,10-epoxyoctadec-12-enyl, 6-octadecynyl, t11-octadecen-9-ynyl, 9-octadecynyl, 6-octadecen-9-ynyl, t10-heptadecen-8-ynyl, 9-octadecen-12-ynyl, t7,t11-octadecadiene-9-ynyl, t8,t10-octadecadiene-12-ynyl, 5,8,11,14-eicosatetraynyl, 2-hydroxytetracosanyl, 2-hydroxy-15-tetracosenyl, 12-hydroxy-9-octadecenyl, and 14-hydroxy-11-eicosenyl.

More preferred are these compounds wherein R" represents 9,12-octadecadienyl, 6,9,12-octadecatrienyl, 8,11,14-eicosatrienyl, 5,8,11,14-eicosatetraenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentaenyl, 4,7,10,13,16,19-docosahexaenyl, 5,8,11-eicosatrienyl, 1,2-dithiolane-3-pentanyl, and 6,8-dithiane octanyl.

Most preferred within said method are the following compounds:
Compound 1: (2'R,3'S,4'R,5'R)-Octadeca-6,9,12-trienoic acid 5'-(2,4-dioxo-3,4-dihydro-2H-pyrimidine-1-yl)-3',4'-dihydroxy-tetrahydrofuran-2'-ylmethyl ester, Compound 2: (2'R,3'S,4'R,5'R)-Octadeca-9,12,15-trienoic acid 5'-(2,4-dioxo-3,4-dihydro-2H-pyrimidine-1-yl)-3',4'-dihydroxy-tetrahydrofuran-2'-ylmethyl ester;

Compound 3: (2'R,3'S,4'R,5'R)-Icosa-5,8,11,14,17-pentaenoic acid 5'-(2,4-dioxo-3,4-dihydro-2H-pyrimidine-1-yl)-3',4'-dihydroxy-tetrahydrofuran-2'-ylmethyl ester, Compound 4: (2'R,3'S,4'R,5'R)-Docosa-4,7,10,13,16,19-hexaenoic acid 5'-(2,4-dioxo-3,4-dihydro-2H-pyrimidine-1-yl)-3',4'-dihydroxy-tetrahydrofuran-2'-ylmethyl ester, Compound 5: (2'R,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester, Compound S5: (2'R,3'S,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester, Compound R5: (2'R,3R,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester, Compound 5': (2'R,3'S,4'R,5'R)-6,8-Dimercapto-octanoic acid 5'-(2,4-dioxo-3,4-dihydro-2H-pyrimidine-1-yl)-3',4'-dihydroxy-tetrahydrofuran-2'-ylmethyl ester, and pharmaceutically acceptable salts of these compounds.

Within said inventive method the compounds of the general formula (I) are administered in a dosage corresponding to an effective concentration in the range of 1-10000 mg, preferably in the range of 1-5000 mg, more preferably in the range of 10-1000 mg, and most preferably in the range of 100-800 mg.

Furthermore, administering at least one compound of the present invention and/or pharmaceutically acceptable salts thereof in combination with further therapeutic drugs, agents, or compounds is also advantageous. Said further therapeutic compounds are selected from the group comprising vitamins and anti-retroviral drugs. Suitable vitamins are vitamin A, B1, B2, B6, B12, C, E, and pharmaceutically acceptable salts thereof.

A further aspect of the present invention is directed to pharmaceutical compositions comprising at least one compound of the general formula (I) and/or pharmaceutically acceptable salts thereof as an active ingredient and a pharmaceutically acceptable carrier, excipient, adjuvant and/or diluents. Said pharmaceutical composition may further comprise additional therapeutically active compounds which may be selected from the group comprising vitamins and anti-retroviral drugs. Especially vitamins like vitamin A, B1, B2, B6, B12, C, E, and pharmaceutically acceptable salts thereof can be further added.

The compounds of the general formula (I) and also the inventive drug combinations can also be administered in form of their pharmaceutically active salts optionally using substantially nontoxic pharmaceutically acceptable carrier, excipients, adjuvants or diluents. The medications of the present invention are prepared in a conventional solid or liquid carrier or diluent and a conventional pharmaceutically-made adjuvant at suitable dosage level in a known way. The preferred preparations and formulations are in administratable form which is suitable for oral application. These administratable forms, for example, include pills, tablets, film tablets, coated tablets, capsules, powders and deposits. Other than oral administratable forms are also possible. The inventive uridine and deoxyuridine compounds or pharmaceutical preparations and formulations containing said compounds may be administered by any appropriate means, including but not limited to injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrally, intracutaneously, intravaginally, intravasally, intranasally, intrabuccally, percutaneously, sublingually, or inhalation or any other means available within the pharmaceutical arts.

Within the disclosed methods the pharmaceutical compositions of the present invention, containing at least one inventive compound of the general formula (I) or pharmaceutically acceptable salts thereof as an active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active ingredient may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethyl-cellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation and intranasal administration may include solutions and solids in powder form, which may be in combination with a pharmaceutically acceptable carrier such as inert compressed gas, e.g. nitrogen. Beside oral administration, inhalation is a preferred form for the application of the compounds of the present invention.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The inventive uridine and deoxyuridine compounds of the present invention may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refers to the active ingredients dispersed or solubilized in a hydrophilic semi-solid matrix.

Powders for constitution refers to powder blends containing the active ingredients and suitable diluents which can be suspended in water or juices.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluent in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluent or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.01 to 10% by weight of the composition, preferably from about 0.05 to 6% by weight, more preferably from about 0.1 to about 4% by weight of the composition, and most preferably from about 0.1 to about 1%.

Techniques for the formulation and administration of the inventive compounds of the present invention may be found in "Remington's Pharmaceutical Sciences" Mack Publishing Co., Easton Pa. A suitable composition comprising at least one compound of the invention and/or pharmaceutically acceptable salts thereof may be a solution of the compound in a suitable liquid pharmaceutical carrier or any other formulation such as tablets, pills, film tablets, coated tablets, dragees, capsules, powders and deposits, gels, syrups, slurries, suspensions, emulsions, and the like.

Toxicity and therapeutic efficacy of the inventive compounds may be determined by standard pharmaceutical, pharmacological, and toxicological procedures in cell cultures or experimental animals for determining the LD50 (the dose lethal to 50% of the population) and the ED50 (the dose therapeutically effective in 50% of the population). The dose ratio between toxic and therapeutic effect is the therapeutic index and can be expressed as the ratio between LD50 and ED50. The dosage of the compound lies preferably within a range of circulating concentrations that include the ED50 with little or no toxicity. The actual amount of the composition administered will be dependent on the subject being treated, on the subject's weight, the severity of the disease, the manner of administration and the judgement of the prescribing physician.

Still a further aspect of the present invention relates to a drug combination comprising at least one fatty acid and/or fatty acid alkyl ester selected from the group comprising linoleic acid, γ-linolenic acid, dihomo-γ-linolenic acid, arachidonic acid, 7,10,13,16-docosatetraenoic acid, 4,7,10,13,16-docosapentaenoic acid, α-linolenic acid, stearidonic acid, 8,11,14,17-eicosatetraenoic acid, EPA, DPA, DHA, Mead acid, eleostearic acid, calendic acid, catalpic acid, stellaheptaenoic acid, taxoleic acid, pinolenic acid, sciadonic acid, retinoic acid, isopalmitic acid, pristanic acid, phytanic acid, 11,12-methyleneoctadecanoic acid, 9,10-methylenehexadecanoic acid, coronaric acid, (R,S)-lipoic acid, (S)-lipoic acid, (R)-lipoic acid, (R,S)-6,8-dithiane octanoic acid, (R)-6,8-dithiane octanoic acid, (S)-6,8-dithiane octanoic acid, tariric acid, santalbic acid, stearolic acid, 6,9-octadecenynoic acid, pyrulic acid, crepenynic acid, heisteric acid, t8,t10-octadecadiene-12-ynoic acid, ETYA, cerebronic acid, hydroxynervonic acid, ricinoleic acid, lesquerolic acid, brassylic acid, thapsic acid, and/or pharmaceutically acceptable salts thereof and/or linoleic acid C1-C7 alkyl ester, γ-linolenic acid C1-C7 alkyl ester, dihomo-γ-linolenic acid C1-C7 alkyl ester, arachidonic acid C1-C7 alkyl ester, 7,10,13,16-docosatetraenoic acid C1-C7 alkyl ester, 4,7,10,13,16-docosapentaenoic acid C1-C7 alkyl ester, α-linolenic acid C1-C7 alkyl ester, stearidonic acid C1-C7 alkyl ester, 8,11,14,17-eicosatetraenoic acid C1-C7 alkyl ester, EPA C1-C7 alkyl ester, DPA C1-C7 alkyl ester, DHA C1-C7 alkyl ester, Mead acid C1-C7 alkyl ester, eleostearic acid C1-C7 alkyl ester, calendic acid C1-C7 alkyl ester, catalpic acid C1-C7 alkyl ester, stellaheptaenoic acid C1-C7 alkyl ester, taxoleic acid C1-C7 alkyl ester, pinolenic acid C1-C7 alkyl ester, sciadonic acid C1-C7 alkyl ester, retinoic acid C1-C7 alkyl ester, isopalmitic acid C1-C7 alkyl ester, pristanic acid C1-C7 alkyl ester, phytanic acid C1-C7 alkyl ester, 11,12-methyleneoctadecanoic acid C1-C7 alkyl ester, 9,10-methylenehexadecanoic acid C1-C7 alkyl ester, coronaric acid C1-C7 alkyl ester, (R,S)-lipoic acid C1-C7 alkyl ester, (S)-lipoic acid C1-C7 alkyl ester, (R)-lipoic acid C1-C7 alkyl ester, (R,S)-6,8-dithiane octanoic acid C1-C7 alkyl ester, (R)-6,8-dithiane octanoic acid C1-C7 alkyl ester, (S)-6,8-dithiane octanoic acid C1-C7 alkyl ester, tariric acid C1-C7 alkyl ester, santalbic acid C1-C7 alkyl ester, stearolic acid C1-C7 alkyl ester, 6,9-octadecenynoic acid C1-C7 alkyl ester, pyrulic acid C1-C7 alkyl ester, crepenynic acid C1-C7 alkyl ester, heisteric acid C1-C7 alkyl ester, t8,t10-octadecadiene-12-ynoic acid C1-C7 alkyl ester, ETYA C1-C7 alkyl ester, cerebronic acid C1-C7 alkyl ester, hydroxynervonic acid C1-C7 alkyl ester, ricinoleic acid C1-C7 alkyl ester, lesquerolic acid C1-C7 alkyl ester, brassylic acid C1-C7 alkyl ester, thapsic acid C1-C7 alkyl ester, together with at least one nucleoside and/or nucleotide compound selected from the group comprising uridine, deoxyuridine, uridine monophosphate, deoxyuridine monophosphate, and/or pharmaceutically acceptable salts thereof.

Preferred is the combination of uridine, deoxyuridine, uridine monophosphate, or deoxyuridine monophosphate with linoleic acid, γ-linolenic acid, dihomo-γ-linolenic acid, arachidonic acid, 7,10,13,16-docosatetraenoic acid, 4,7,10,13,16-docosapentaenoic acid, α-linolenic acid, stearidonic acid, 8,11,14,17-eicosatetraenoic acid, EPA, DPA, DHA, Mead acid, (R,S)-lipoic acid, (S)-lipoic acid, (R)-lipoic acid, (R,S)-6,8-dithiane octanoic acid, (R)-6,8-dithiane octanoic acid, (S)-6,8-dithiane octanoic acid, eleostearic acid, catalpic acid, calendic acid, docosaheptadecanoic acid, taxoleic acid, pinolenic acid, sciadonic acid, retinoic acid and/or pharmaceutically acceptable salts thereof, and/or linoleic acid C1-C7 alkyl ester, γ-linolenic acid C1-C7 alkyl ester, dihomo-γ-linolenic acid C1-C7 alkyl ester, arachidonic acid C1-C7 alkyl ester, 7,10,13,16-docosatetraenoic acid C1-C7 alkyl ester, 4,7,10,13,16-docosapentaenoic acid C1-C7 alkyl ester, α-linolenic acid C1-C7 alkyl ester, stearidonic acid C1-C7 alkyl ester, 8,11,14,17-eicosatetraenoic acid C1-C7 alkyl ester, EPA C1-C7 alkyl ester, DPA C1-C7 alkyl ester, DHA C1-C7 alkyl ester, Mead acid C1-C7 alkyl ester, (R,S)-lipoic acid C1-C7 alkyl ester, (S)-lipoic acid C1-C7 alkyl ester, (R)-lipoic acid C1-C7 alkyl ester, (R,S)-6,8-dithiane octanoic acid C1-C7 alkyl ester, (R)-6,8-dithiane octanoic acid C1-C7 alkyl ester, (S)-6,8-dithiane octanoic acid C1-C7 alkyl ester, eleostearic acid C1-C7 alkyl ester, catalpic acid C1-C7 alkyl ester, calendic acid C1-C7 alkyl ester, docosaheptadecanoic acid C1-C7 alkyl ester, taxoleic acid C1-C7 alkyl ester, pinolenic acid C1-C7 alkyl ester, sciadonic acid C1-C7 alkyl ester, and/or retinoic acid C1-C7 alkyl ester.

More preferred is a drug combination comprising uridine, deoxyuridine, uridine monophosphate, or deoxyuridine monophosphate with γ-linolenic, α-linolenic, EPA, DHA, (R,S)-6,8-dithiane octanoic acid, (R)-6,8-dithiane octanoic acid, (S)-6,8-dithiane octanoic acid, (R,S)-lipoic acid, (S)-lipoic acid, and/or (R)-lipoic acid, and/or pharmaceutically acceptable salts thereof, and/or γ-linolenic C1-C7 alkyl ester, α-linolenic acid C1-C7 alkyl ester, EPA C1-C7 alkyl ester, DHA C1-C7 alkyl ester, (R,S)-6,8-dithiane octanoic acid C1-C7 alkyl ester, (R)-6,8-dithiane octanoic acid C1-C7 alkyl ester, (S)-6,8-dithiane octanoic acid C1-C7 alkyl ester, (R,S)-lipoic acid C1-C7 alkyl ester, (S)-lipoic acid C1-C7 alkyl ester, and/or (R)-lipoic acid C1-C7 alkyl ester.

Most preferred is a drug combination of (R,S)-lipoic acid, (S)-lipoic acid, (R)-lipoic acid, (R,S)-6,8-dithiane octanoic acid, (R)-6,8-dithiane octanoic acid, and/or (S)-5,8-dithiane octanoic acid, and/or (R,S)-lipoic acid C1-C7 alkyl ester, (S)-lipoic acid C1-C7 alkyl ester, (R)-lipoic acid C1-C7 alkyl ester, (R,S)-6,8-dithiane octanoic acid C1-C7 alkyl ester, (R)-6,8-dithiane octanoic acid C1-C7 alkyl ester, and/or (S)-6,8-dithiane octanoic acid C1-C7 alkyl ester with uridine, deoxyuridine, uridine monophosphate, or deoxyuridine monophosphate, and/or pharmaceutically acceptable salts thereof.

Suitable alcohols for the formation of the C1-C7 alkyl ester of the above mentioned fatty acids are: methanol, ethanol, propanol, iso-propanol, butanol, sec-butanol, tert-butanol, iso-butanol, pentanol, iso-pentanol, cyclopentanol, hexanol, cyclohexanol, heptanol.

Said drug combination may further comprise suitable pharmaceutically acceptable carriers, excipients, adjuvant and/or diluents as described above in detail.

Another aspect of the present invention is related to the use of said drug combination for prophylaxis and/or treatment of diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, Chlamydia pneumoniae, depression, obesity, stroke, pain, and retroviral infections (HIV, AIDS), including opportunistic infections. Furthermore, the drug combination comprising at least one compound of the general formula (I) and/or pharmaceutically acceptable salts thereof can be used as stimulant drug, especially for the treatment of attention-deficit disorder, narcolepsy, obesity, anxiety, depression, epilepsy, psychosis and sleeping disorders and to stimulate specific body functions, especially of the central nervous system.

Said drug combination may also be used for the manufacture of a pharmaceutical formulation or preparation for prophylaxis and/or treatment of diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, *Chlamydia pneumoniae*, depression, obesity, stroke, pain, and retroviral infections (HIV, AIDS), including opportunistic infections. Said pharmaceutical formulation comprising the drug combination is also useful as stimulant in order to treat attention-deficit disorder, narcolepsy, obesity, anxiety, depression, epilepsy, psychosis and sleeping disorders and to stimulate specific body functions, especially of the central nervous system.

Said pharmaceutical formulation or preparation can be manufactured in a form suitable for intravenous, intraperitoneal, intramuscular, subcutaneous, oral, rectal, epithelial, intestinal, transdermal, topical, intradermal, intragastral, intracutan, intravaginal, intravasal, intranasal, intrabuccal, percutan, sublingual, or any other application. Furthermore, said pharmaceutical formulation may also comprise at least one substantially nontoxic pharmaceutically acceptable carrier, excipients, adjuvants or diluents as described above in detail.

The inventive drug combination is administered in a dosage corresponding to an effective concentration in the range of 1-15000 mg, preferably 1-8000 mg, more preferably 1-5000 mg, even more preferably in the range of 10-2000 mg, and most preferably in the range of 100-1000 mg.

Another advantageous aspect of the present invention is directed to said drug combination which further comprises another therapeutic agent or compound wherein said further therapeutic compound is selected from the group comprising vitamins and anti-retroviral drugs. Suitable vitamins are vitamin A, B1, B2, B6, B12, C, E, and pharmaceutically acceptable salts thereof.

Also revealed for the first time is a method for preventing and/or treating diabetes mellitus Type I and Type II, inflammation, cancer, necrosis, gastric ulcers, neurodegenerative diseases (Alzheimer's disease, Parkinson's disease), neuropathic diseases, neuropathic pain and polyneuropathy, peripheral and/or central nerve diseases, degradation of the peripheral and/or central nerve system, heavy metal poisoning, ishemic diseases and ishemic heart disease, liver diseases and dysfunction of liver, allergies, cardiovascular diseases, *Chlamydia pneumoniae*, depression, obesity, stroke, pain, and retroviral infections (HIV, AIDS), including opportunistic infections, in a mammal, including a human, which comprises administering to said mammal an amount of said drug combination effective to treat said disease or dysfunction. In addition thereto, a method for stimulating the organism and specific body functions of said mammal is disclosed comprising administering to said mammal an amount of said drug combination effective to stimulate the organism and said specific body functions.

Within said inventive method the drug combination is administered in a dosage corresponding to an effective concentration in the range of 1-30000 mg, preferably in the range of 10-20000 mg, more preferably in the range of 50-15000 mg, even more preferably in the range of 100-10000 mg, and most preferably in the range of 1000-6000 mg.

Compound 1: (2'R,3'S,4'R,5'R)-Octadeca-6,9,12-trienoic acid 5'-(2,4-dioxo-3,4-dihydro-2H-pyrimidine-1-yl)-3',4'-dihydroxy-tetrahydrofuran-2'-ylmethyl ester, Compound 2: (2'R,3'S,4'R,5'R)-Octadeca-9,12,15-trienoic acid 5'-(2,4-dioxo-3,4-dihydro-2H-pyrimidine-1-yl)-3',4'-dihydroxy-tetrahydrofuran-2'-ylmethyl ester, Compound 3: (2'R,3'S,4'R,5'R)-Icosa-5,8,11,14,17-pentaenoic acid 5'-(2,4-dioxo-3,4-dihydro-2H-pyrimidine-1-yl)-3',4'-dihydroxy-tetrahydrofuran-2'-ylmethyl ester, Compound 4: (2'R,3'S,4'R,5'R)-Docosa-4,7,10,13,16,19-hexaenoic acid 5'-(2,4-dioxo-3,4-dihydro-2H-pyrimidine-1-yl)-3',4'-dihydroxy-tetrahydrofuran-2'-ylmethyl ester, Compound 5: (2'R,3'S,4'R,5'R)-5-[1,2]Dithiolan-3-yl-pentanoic acid 5'-(2,4-dioxo-3,4-dihydro-2H-pyrimidine-1-yl)-3',4'-dihydroxy-tetrahydrofuran-2'-ylmethyl ester, and Compound 5': (2'R,3'S,4'R,5'R)-6,8-Dimercapto-octanoic acid 5'-(2.4-dioxo-3,4-dihydro-2H-pyrimidine-1-yl)-3',4'-dihydroxy-tetrahydrofuran-2'-ylmethyl ester.

Figure 1A:
FIGS. 1*a*, 1*b* and 1*c* show a group of selected fatty acids.
Figure 1A:
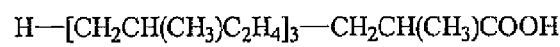
Figure 1A:
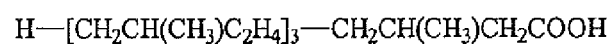
Figure 1A:
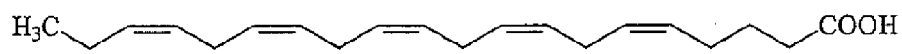
Figure 1A:
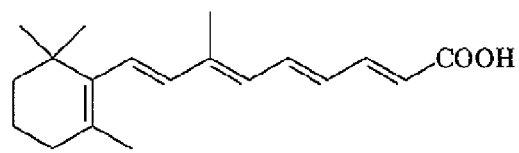
Figure 1B:
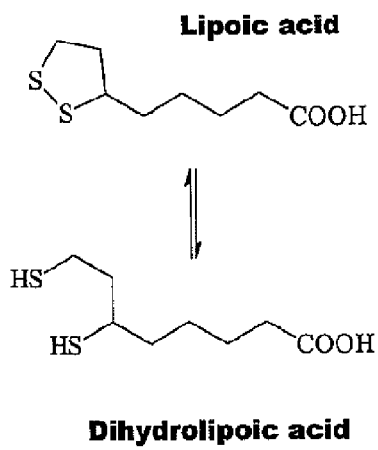
Figure 1B:
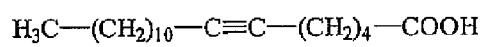
Figure 1B:
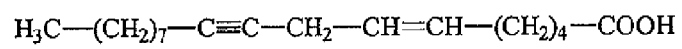
Figure 1B:
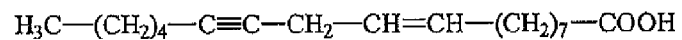
Figure 1B:
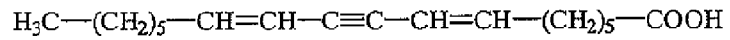
Figure 1C:
Figure 1C:
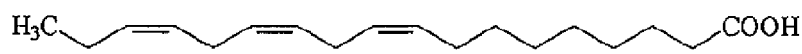
Figure 1C:
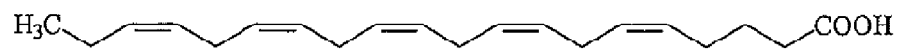
Figure 1C:
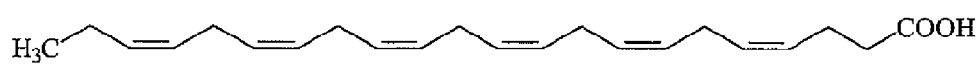
Figure 2:
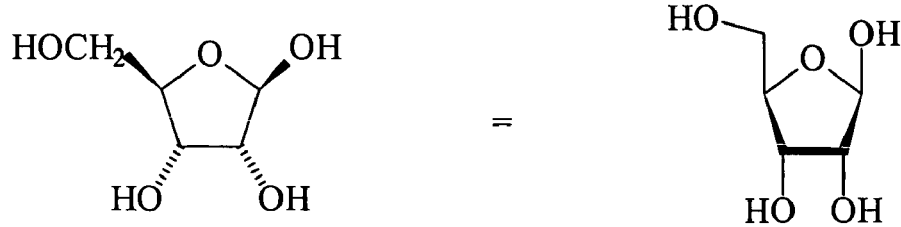
FIG. 2 shows ribose, deoxyribose and the nucleosides uracil, cytosine, and thymine, the basic residues of the compounds of the general formula (I)
Figure 2:
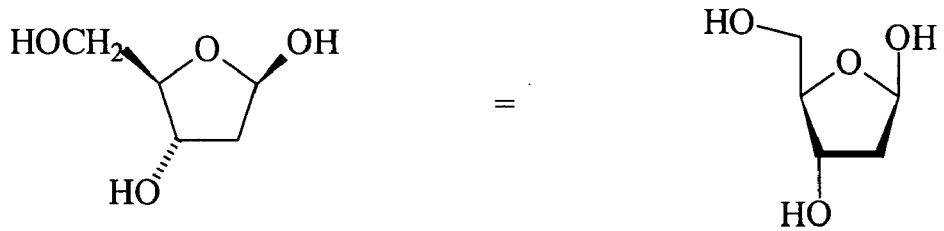
Figure 2:
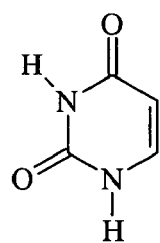
Figure 2:
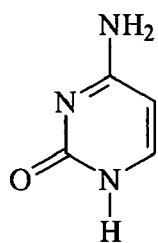
Figure 2:
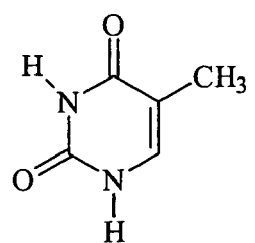
Figure 3:
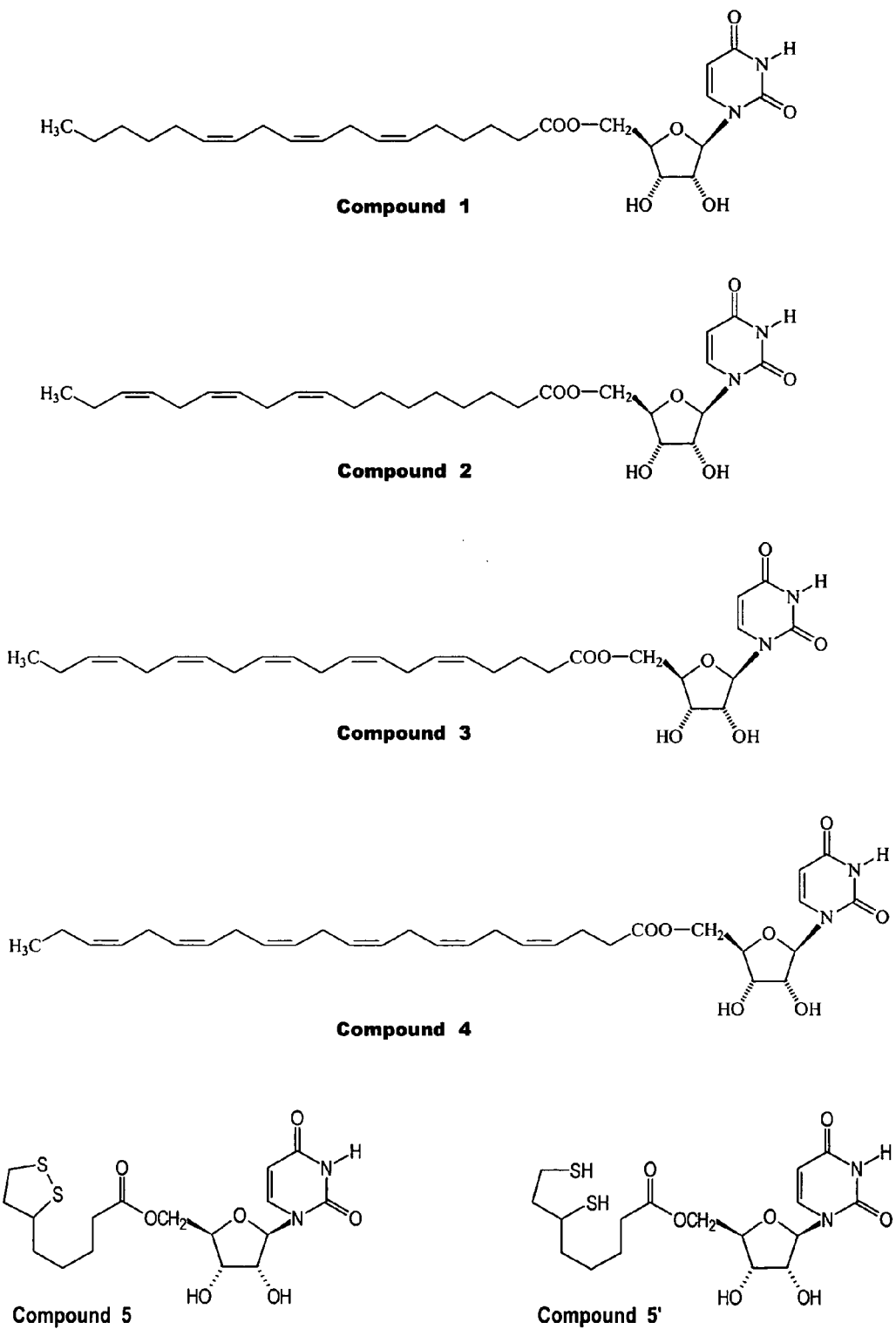
FIG. 3 discloses the structures of six highly active compounds of the general formula (I)
Figure 4:
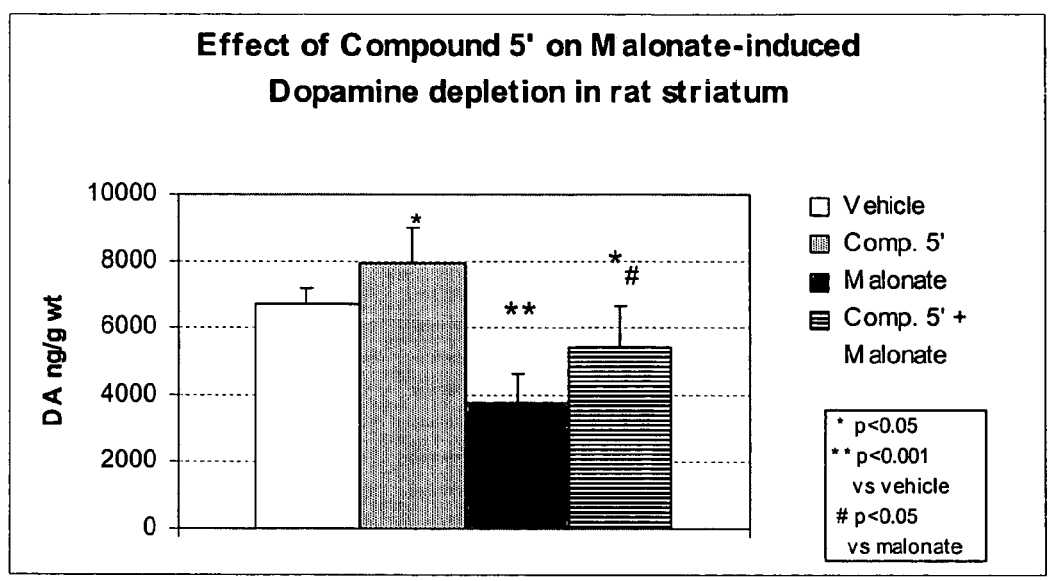
Figure 5A:
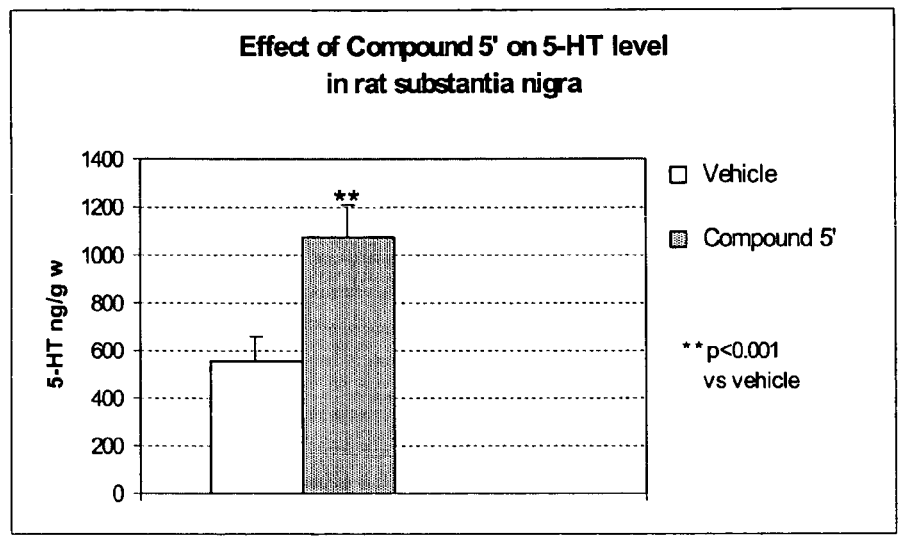
Figure 5B:
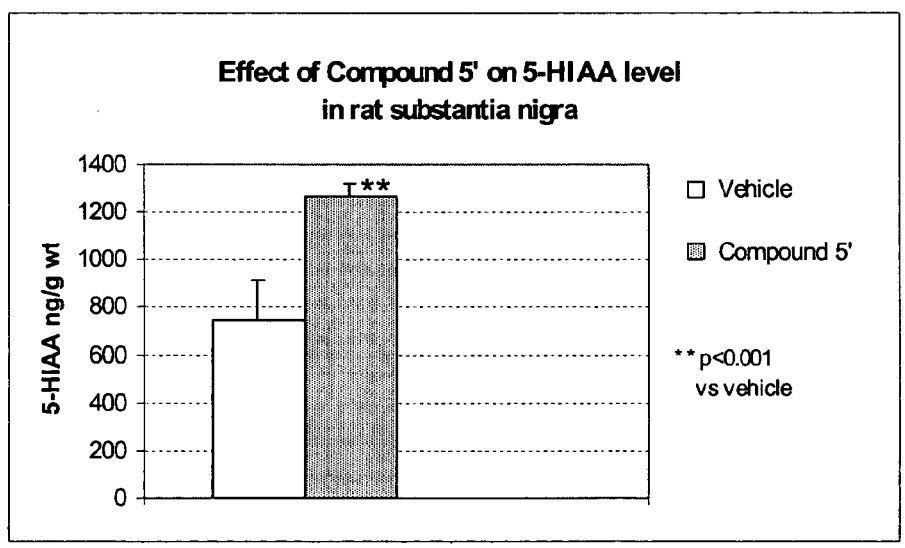

FIG. 4 shows the effect of compound 5' on the dopamine concentration in rat striatum. The harmful malonate-induced dopamine depletion in rat striatum can almost be compensated by the administration of relatively low concentrations of compound 5';

FIG. 5*a* shows that compound 5' is able to significantly increase the 5-HT concentration in rat substantia nigra;

FIG. 5*b* shows that compound 5' is able to significantly increase the 5-HIAA level in rat substantia nigra.

EXAMPLES

Example 1

General Procedure for Esterification 1 mol equivalent of fatty acid was dissolved in a polar aprotic solvent. Preferred solvents are dichloromethane, chloroform, or ethers such as THF. 0.1-2.0 mol equivalents, preferably 0.5 to 1.2 mol equivalents, of dicyclohexylcarbodiimide (DCC) preferably dissolved in the reaction solvent were added in one portion. After a couple of minutes 1.0 mol equivalent of a protected nucleoside or deoxynucleosid were given to the solution and after another couple of minutes catalytic or semi-equimolar amounts of dimethyl aminopyridine (DMAP) were added. The reaction mixture was stirred for 10 to 20 hours under exclusion of light. Purification of the obtained products were performed according to standard procedures well known in the state of the art.

Example 2

General Procedure for Ketal Cleavage

The cleavage of ketals is performed under acidic conditions. For example, benzylsulfonic acids or other organic acids dissolved in organic solvents may be used. The best results were obtained with acetic acid and most preferably with 80% acetic acid. The reaction was normally carried out at elevated temperature, preferably between 80° C. and 100° C. for several hours, preferably 2 to 6 hours depending on the stability of the reactants. After neutralization the purification of the compound according to general formula (I) were performed according to standard procedures well known to a skilled person.

Example 3

Synthesis of Compound 3

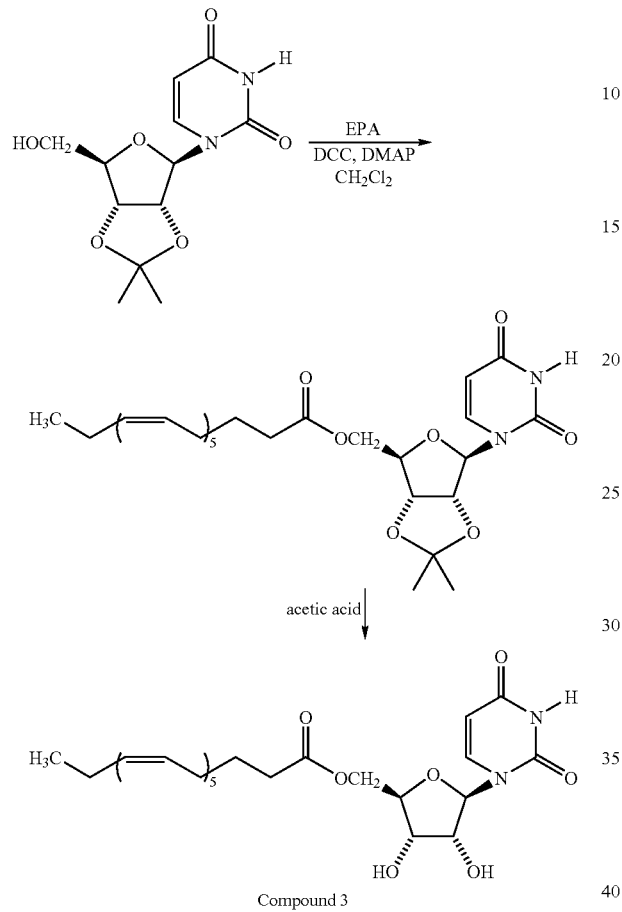

Compound 3

Step 1: Esterification 2.00 g (6.61 mmol) EPA were dissolved under nitrogen in 10 ml dichloromethane. 1.38 g (1.16 mmol) DCC dissolved in 20 ml dichloromethane were added and after 5 minutes 1.88 g (6.61 mmol) ketal protected uridine as obtained from step 1 according to example 5 were added. After another 5 minutes 25 mg DMAP were given to the solution. The reaction was stirred over night at room temperature in the dark. The resulting solution was diluted with 30 ml MTBE (methyl tert-butyl ether), filtered, and concentrated. The brown and oily remainder was purified by column chromatography using hexane : isopropanol (5:1) as eluent. A colorless oil was obtained.

Yield: 3.42 g (6.01 mmol, 91% th.)

Step 2: Ketal Cleavage 3.10 g (5.45 mmol) ketal protected compound 3 as obtained from step 1 were dissolved in 40 ml 80% acetic acid and heated up to approximately 95° C. for 4.5 hours. The acetic acid was removed under reduced pressure and the remainder was redissloved in 50 ml ethyl acetate, washed with saturated NaHCO$_3$ solution, twice with brine, dried over Na$_2$SO$_4$, and concentrated. A brown oil was obtained which was purified by column chromatography using dichloromethane : methanol (10:1) as eluent. A light yellow and highly viscous oil was obtained.

Yield: 1.52 g (2.88 mmol, 53% th.)

Compound 3:

MS (m/z(%)): 528 (2,37) M$^+$; 113 (100)

$^1$H-NMR (400 MHz; CDCl$_3$):

δ=0.98 (t, 3H), 1.69-1.76 (m, 2H), 2.05-2.16 (m, 4H), 2.35-2.39 (m, 2H), 2.79-2.87 (m, 8H), 4.12-4.14 (m, 1H), 4.25-4.32 (m, 2H), 4.35-4.44 (m, 2H), 5.28-5.46 (m, 10H), 5.75 (d, 1H), 5.82 (d, 1H), 7.62 (d, 1H), 10.15 (s, 1H)

$^{13}$C-NMR (100.6 MHz; CDCl$_3$):

δ=14.24, 20.54, 24.67, 24.82, 25.55, 25.63, 26.45, 32.12, 33.45, 63.20, 70.22, 75.01, 82.23, 91.27, 102.48, 127.03, 127.89, 128.05, 128.34, 128.57, 128.61, 128.72, 128.76, 129.24, 132.05, 139.71, 151.18, 163.63, 173.92

Compounds 1 and 2 have been synthesized according to the above-mentioned procedure wherein EPA was replaced either by γ-linolenic acid or α-linolenic acid. Yields are over 90% for step 1 and about 50% for step 2.

Example 4

Synthesis of Compound 4

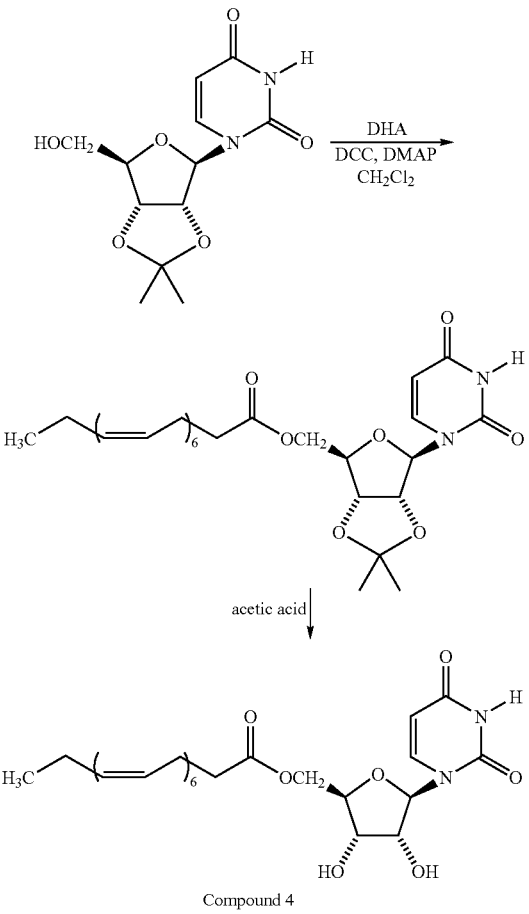

Compound 4

Step 1: Esterification 2.20 g (6.70 mmol) DHA were dissolved under nitrogen in 20 ml dichloromethane. 1.40 g (6.78 mmol) DCC dissolved in 20 ml dichloromethane were added and after 5 minutes 1.90 g (6.69 mmol) ketal protected uridine as obtained from step 1 according to example 5 were added. After another 5 minutes 40 mg DMAP were given to the solution. The reaction was carried out under exclusion of light. The resulting solution was diluted with 20 ml MTBE, filtered, washed with 10 ml MTBE and concentrated. The remainder was purified by column chromatography using hexane: ethyl acetate (2:1) as eluent. A colorless oil was obtained.

Yield: 3.15 g (5.30 mmol, 79% th.)

Step 2: Ketal Cleavage 3.10 g (5.21 mmol) ketal protected compound 4 as obtained from step 1 were dissolved in 125 ml 80% acetic acid and heated up to approximately 95° C. The reaction was detected by TLC or HPLC. After two hours at 95° C. about 90% of the starting material was converted to compound 4. The acetic acid was removed under reduced pressure and the remainder was redissloved in 20 ml ethyl acetate, washed with saturated NaHCO$_3$ solution, twice with brine, dried over Na$_2$SO$_4$, and concentrated. A brown oil was obtained which was purified by column chromatography using dichloromethane: isopropanol (10:1) as eluent. A light yellow and highly viscous oil was obtained.

Yield: 1.20 g (2.17 mmol, 42% th.)

Compound 4:

MS (m/z(%)): 555 (2,37) M$^+$; 113 (100)

$^1$H-NMR (400 MHz; CDCl$_3$):

δ=0.98 (t, 3H), 2.05-2.12 (m, 2H), 2.40-2.45 (m, 4H), 2.80-2.89 (m, 1H), 3.52 (d, 1H), 4.13-4.16 (m, 1H), 4.254.32 (m, 2H), 4.364.44 (m, 2H), 5.15 (d, 1H), 5.29-5.47 (m, 12H), 5.75 (d, 1H), 5.82 (d, 1H), 7.62 (d, 1H), 10.10 (s, 1H)

$^{13}$C-NMR (100.6 MHz; CDCl$_3$):

δ=14.24, 20.55, 22.12, 22.62, 25.32, 25.55, 25.61, 25.65, 34.00, 63.24, 70.23, 75.04, 82.26, 91.13, 102.47, 127.03, 127.40, 127.88, 128.05, 128.07, 128.33, 128.49, 128.60, 129.86, 132.05, 139.67, 151.19, 163.56, 172.61

Example 5

Synthesis of Compound 5

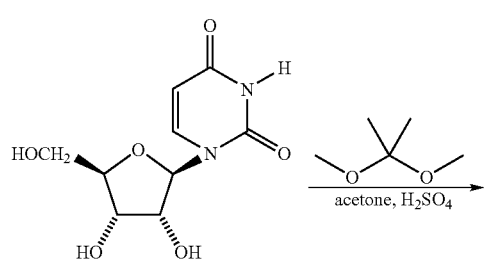

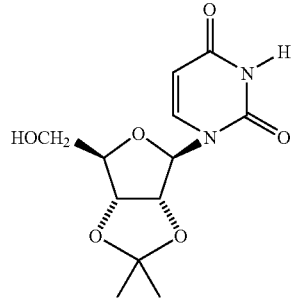

Step 1: Ketalization 27.7 g uridine were dissolved under nitrogen in 250 ml anhydrous acetone and 11.8 g 2,2-dimethoxypropane. After addition of 0.3 ml conc. sulfuric acid the reaction mixture was stirred for about 20 h at room temperature. During this time a voluminous fine precipitation was formed. After filtration the remaining solution was treated with 2 ml triethylamine in 80 ml dichlormethane and was subsequently washed thoroughly.

Yield: 21.9 g (77.0 mmol, 68% th)

Melting point: 159-160° C.

The yield can be further increased by reducing the volume of acetone for about one third, and by adding heptane as an anti-solvent, and by cooling the mixture to 0-5° C. prior to filtration. Yields in the range of 80-85% can be obtained.

Because of cost reasons it has been demonstrated that the anhydrous acetone can be replaced by bulk acetone having a water content of 0.1% (w/w) without showing an effect on the yield.

Step 2: Esterification 4.00 g DL-α-lipoic acid were dissolved under nitrogen in 50 ml dichlormethane and 4.00 g DCC (dicyclohexylcarbodiimide) dissolved in 70 ml dichlormethane were added. After 5 minutes 5.51 g of the ketal as obtained from step 1 were given to the solution and after another 5 minutes 150 mg DMAP (dimethylaminopyridine) were added. The solution was stirred over night at room temperature, diluted with 100 ml MTBE (methyl tert-butyl ether) and filtered. The solvent was removed under vacuum and the remaining oil was purified by column chromatography on silica using hexane: ethyl acetate (1:2) as eluent. A yellow viscous oil was obtained.

Yield: 8.06 g (17.1 mmol, 88% th)

The step 2 reaction can also be carried out in ethyl acetate having the advantage that the reaction product can without purification directly subjected to the reaction conditions of step 3. After stirring the reaction over night at room temperature the slight excess of DCC is hydrolysed to DCU (dicyclohexyl urea) by an aqueous 10% citric acid wash and the excess of DL-α-lipoic acid is easily removed by washing with an aqueous $NaHCO_3$-solution. The DCU is removed during work-up by filtration. Yields are between 50 and 90% th depending on scale and solvent.

Beside DCC/DMAP also pivaloyl chloride/DMAP has been examined as effective coupling agents. Solvents like toluene or ethers such as THF or dioxane can be used instead of dichloromethane. Instead of DCC N,N'-carbonyl diimidazole or chloroformic acid isobutyl ester may be used.

Step 3: Deprotection 11.7 g ketal protected compound 5 as obtained from step 2 were stirred 5.5 h in 300 ml acetic acid at a temperature of about 95° C. Thereafter, the acetic acid was removed under vacuum and the remainder was redissolved in 150 ml ethyl acetate. Said solution was washed two times with 70 ml saturated $NaHCO_3$-solution each and subsequently two times with 100 ml saturated NaCl-solution each. The solution was dried over $Na_2SO_4$ and the solvent was nearly removed completely (the concentration to dryness should be avoided). The pale remainder was redissolved in 150 ml ethyl acetate and optionally treated with ultrasonic for 2-3 minutes while a yellow precipitate was formed. The precipitate (compound 5) was separated by filtration, washed with ethyl acetate and dried. Beside ethyl acetate, n-BuOH, toluene, 1-pentanol, acetonitril or mixtures of these solvents have been examined as alternative precipitation solvents.

Yield: 7.42 g (17.2 mmol, 69% th)

Compound 5:

Melting point: 95-97° C.

Purity: >98% (HPLC)

MS (m/z(%)): 432 (7.9) $M^+$, 113 (100)

$^1$H-NMR (400 MHz, $d_4$-methanol):

δ=1.41-1.50 (m, 2H), 1.57-1.72 (m, 4H), 1.82-1.90 (m, 1H), 2.37-2.47 (m, 3H), 3.04-3.18 (m, 2H), 3.51-3.57 (m, 1H), 4.06-4.19 (m, 3H), 4.29-4.37 (m, 2H), 5.71 (d,1H), 5.80 (d, 1H), 7.66 (d, 1H).

$^{13}$C-NMR (100.6 MHz, $d_4$-methanol):

δ=25.7, 29.7, 34.7, 35.7, 39.3, 41.3, 57.5, 64.6, 71.2, 75.2, 82.9, 91.8, 102.9, 142.3, 152.2, 166.0, 174.8

Example 6

Synthesis of compound S-5

Compound S-5 was synthesized according to the reaction procedures as outlined in example 5. Instead of DL-α-lipoic acid the enantiomerically pure S-α-lipoic acid was used.

Compound S-5:

Melting point: 109-110° C.

$^1$H-NMR (400 MHz, $d_6$-DMSO):

δ=1.30-1.40 (m, 2H), 1.47-1.56 (m, 3H), 1.59-1.68 (m, 1H), 1.77-1.87 (m, 1H), 2.30-2.40 (m, 3H), 3.04-3.18 (m, 2H), 3.53-3.60 (m, 1H), 3.88-3.97 (m, 2H), 4.02-4.06 (m, 1H), 4.13-4.23 (m, 2H), 5.21 (d, 1H), 5.40 (d, 1H), 5.62 (d, 1H), 5.71 (d, 1H), 7.57 (d,1H).

Example 7

Synthesis of Compound R-5

Compound R-5 was synthesized according to the reaction procedures as outlined in example 5. Instead of DL-α-lipoic acid the enantiomerically pure R-α-lipoic acid was used.

Compound R-5:

Melting point: 88-89° C.

$^1$H-NMR (400 MHz, $d_6$-DMSO):

δ=1.30-1.40 (m, 2H), 1.47-1.56 (m, 3H), 1.59-1.68 (m, 1H), 1.79-1.86 (m, 1H), 2.30-2.41 (m, 3H), 3.04-3.17 (m, 2H), 3.53-3.60 (m, 1H), 3.88-3.97 (m, 2H), 4.02-4.06 (m, 1H), 4.13-4.24 (m, 2H), 5.21 (d, 1H), 5.40 (d, 1H), 5.62 (d, 1H), 5.71 (d, 1H), 7.58 (d,1H), 11.27 (s,1H).

Example 8

Synthesis of Compound 5'

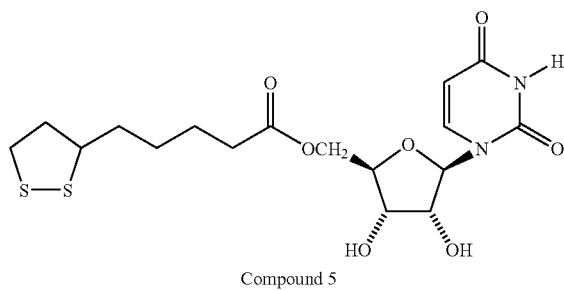

Compound 5

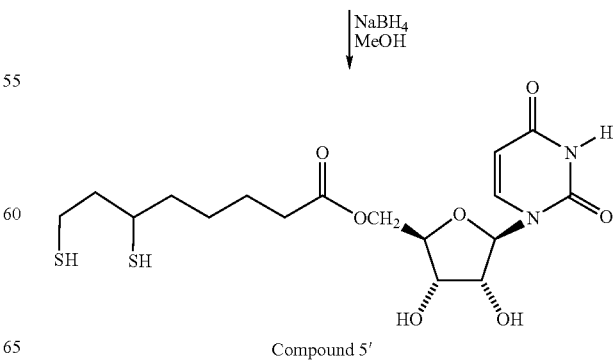

Compound 5'

2.28 g (5.27 mmol) of compound 5 were dissolved in 40 ml methanol under an inert atmosphere. The solution was cooled to 0° C. and 2.50 g (66.1 mmol) sodium borhydride was added over 15 minutes in small portions. During $NaBH_4$ addition the yellow solution became colourless. After complete addition of sodium borhydride the solution was stirred for 45 minutes, diluted with 50 ml water and acidified with concentrated HCl to pH=1.50 ml chloroform were added and the organic layer was separated, washed twice with 10 ml brine, dried over $Na_2SO_4$ and concentrated. After purification compound 5' was obtained as colorless oil.

Yield: 1.63 g (3.75 mmol, 71% th.)

Compound 5:

MS (m/z(%)): 401 (18.0) $M^+$-$H_2S$; 113 (100)

$^1$H-NMR (400 MHz, $d_6$-DMSO):

δ=1.30-1.79 (m, 7H), 1.32-1.43 (m, 2H), 1.85-1.94 (m, 1H), 2.33-2.40 (m, 2H), 2.61-2.76 (m, 2H), 2.88-2.96 (m, 1H), 4.15 (s, br., 1H), 4.26 (s, br., 2H), 4.32-4.42 (m, 2H), 5.75 (d, 1H), 5.83 (d, 1H), 7.58 (d, 1H), 10.32 (s, br., 1H).

$^{13}$C-NMR (100.6 MHz, $d_6$-DMSO):

δ=25.7, 29.7, 34.7, 35.7, 39.3, 41.3, 57.5, 64.6, 71.2, 75.2, 82.9, 91.8, 102.9, 142.3, 152.2, 166.0, 174.8

Example 9

Diabetes and Polyneuropathy

The model used to determine the effect of the compounds of the present invention on treating diabetes and/or polyneuropathy comprises the use of in-vitro Hippocampus cuts for detecting the over-sensitiveness of pyramid cells due to the enhancement of the glucose concentration. Said over-sensitiveness could be antagonized dose-dependent by the use of a compound of the general formula (I).

The Hippocampus cuts of rats present a validated model for determination of interaction between a drug substance which is in direct contact with neuronal tissue. The interaction between a pharmaceutically active compound and the brain tissue can be examined directly, because of the maintenance of the three dimensional structure of the tissue within the in-vitro Hippocampus cut. Said compounds act on a special population of nerve cells, the pyramid cells of the Hippocampus. It is known that the synapse between pyramid cells and Schaffer-collaterals (which can be electrically stimulated) use the neurotransmitter glutamate for the process of signal transduction. The result of the electric stimulation, the so called population spike, represents the amount of activated pyramid cells. Other known models allow the in-vitro determination of a neuronal network only within a time frame of up to 8 hours. The advantage of this model is that neuronal network can be analyzed in-vitro over a much longer period after chemical or electric provocation of the cells. The cells are brought to an elevated level of stimulation which allows a long term measurement of pharmacologically active compounds under patho-physiologic conditions (W. Dimpfel et al., Antimicrobial Agents and Chemotherapy 1991, 1142-1146; W. Dimpfel et al., Eur. J. Med. Res. 1996, 1, 523-527).

Materials & Methods

Within the present method the level of stimulation was elevated by the use of an increased concentration of glucose in the superfusion medium in order to measure the antagonistic effect of the compounds of the present invention. Because of the fact that α-lipoic acid had been applied to this method (W. Dimpfel et al., Eur. J. Med. Res. 1996, 1, 523-527), compound 5' was selected as a close related compound in order to produce reasonable results when comparing α-lipoic acid and uridine with compound 5'. Thus, α-lipoic acid and uridine were selected as reference.

21 adult male CD rats had been used within the present studies. The Hippocampus was isolated after anesthetization and exsanguination of the test animals. The middle part of the Hippocampus was fixed by means of a glue in phosphate-buffered saline (NaCl: 124 mM, KCl: 5 mM, $CaCl_2$: 2 mM, $MgSO_4$: 2 mM, $NaH_2PO_4$: 1.25 mM, $NaHCO_3$: 26 mM, glucose: 10 mM; control solution: ACSF; Carl Roth, Karlsruhe, Germany). The Hippocampus was subsequent cut into slides of 400 μM by means of a Vibratom (Rhema Labortechnik). The Hippocampus cuts were stored at least one hour before the test runs in an incubation chamber under carbogen (S. J. Schiff, G. G. Somjen, Brain Research 1985, 345, 279-284).

The experiment was carried out in a so called "Base Unit with Haas Top" (Medical Systems Corporation, U.S.A.) at a temperature of 35° C. according to the protocol of H. L. Haas and R. W. Greene (Neurotransmitter and cortical function; ed. M. Avoli, T. A. Reader, R. W. Dykes and P. Gloor, pp. 483-494, Plenum Publishing Corp.). The Hippocampus cut was placed on a piece of gauze and perfused by means of peristaltic pumps. The test apparatus was flushed with carbogen (flow rate: 200 ml per hour) in order to maintain the necessary oxygen supply.

The $CA_2$-region was stimulated by means of a stimulus generator (laboratory computer, Pro Science) and a bipolar concentric steel electrode (Rhodes Medical Systems, U.S.A.). A pulse width of 200 μs was used and the amperage was constantly kept at 200 μA. The stimulus generator released four single stimulation signals within intervals of 20 seconds which released a total number of four population spikes in the Hippocampus cut. An average value of the four amplitudes of the spikes was calculated.

Results

The previous findings that α-lipoic acid is able to antagonize the over-sensitiveness induced by an increased glucose concentration could be reproduced (W. Dimpfel et al., Eur. J. Med. Res. 1996, 1, 523-527). Furthermore, uridine was used as a second reference. The electric reply of the hippocampal pyramid cells in form of the population spike was increased for about 160% during the presence of 30 mM glucose compared to the initial value of approximately 1 mV. All three substances, α-lipoic acid, uridine and compound 5', were able to reduce dose-dependent the elevated stimulation level.

It could be demonstrated that compound 5' was active within a range of 1-25 μM while said rang of concentration was extended to about 100 μM for uridine. α-Lipoic acid shown a nearly linear effect up to a concentration of 400 μM. Thus, the calculated $IC_{50}$-values for compound 5' are 5 μM, for uridine 40 μM, and for α-lipoic acid is the $IC_{50}$-value approximately 200 μM.

A direct comparison of the effect of compound 5' with α-lipoic acid and uridine on the enhancement of the glucose-induced over-sensitiveness could be performed by the use of the above described model. The elevated level of over-sensitiveness of the hippocampal pyramid cells could be most effectively treated with compound 5' while uridine and α-lipoic acid showed only weaker effects.

Thus, it can be stressed that compound 5' is able to significantly reduce the increased over-sensitiveness and, therefore, the compounds according to general formula (I) can be used as pharmaceutically effective agents to treat diabetes and polyneuropathy.

Example 10

Diabetes and Polyneuropathy

According to the procedure and the model as outlined in Example 9 also S-5 and R-5 were tested and the test results were compared to those of uridine and α-lipoic acid.

As a reply to the electric stimulation the population spike of the activated pyramid cells was measured. The amplitude of the population spike represents the amount of activated pyramid cells. The electric reply of the hippocampal pyramid cells in form of the population spike was increased for about 160% to 170% during the presence of 30 mM glucose compared to the initial value of approximately 1 mV. The amplitude of the population spike was measured in μV and the mean was calculated of at least three measured amplitudes.

It could be demonstrated that compound R-5 was active within a range of 1-15 pM while compound S-5 was active within the range of 1-10 μM. As described above, uridine showed activity within the concentration range of 1-100 μM and α-lipoic acid showed a nearly linear effect up to a concentration of 400 μM. The calculated $IC_{50}$-value for compound S-5 is 4 μM, for R-5 8 μM, for uridine 40 μM, and for α-lipoic acid is the $IC_{50}$-value approximately 200 μM.

A comparison of the effect of compounds 5', S-5, and R-5 with $IC_{50}$-values within the range of 4-8 μM with α-lipoic acid ($IC_{50}$-value≈200 pM) and uridine ($IC_{50}$-value≈40 μM) on the enhancement of the glucose-induced over-sensitiveness could be performed by the use of the above described model. Said comparison proves that the compounds of the present invention are capable of reducing the elevated level of over-sensitiveness of the hippocampal pyramid cells in a very similar manner while uridine and α-lipoic acid showed much weaker effects.

Thus, it can be stated that the compounds of the present invention are able to significantly reduce the increased over-sensitiveness of the pyramid cells and, therefore, are pharmaceutically effective agents to treat diabetes and polyneuropathy.

Example 11

Neuroprotective Effects

As demonstrated by this example, the compounds of the present invention show neuroprotective potency. The neuroprotective effects of α-lipoic acid and more pronounced of dihydrolipoic acid are well known (P. Wolz, J. Kriegstein, Lipoic Acid in Health and Disease, New York, Basel, Hong Kong, Marcel Dekker Inc., 1997, pp. 205-225). Thus, dihydrolipoic acid was chosen as a positive control for comparison reasons. The most similar compound to dihydrolipoic acid of the present invention is compound 5'. The mouse model as described below was used in order to examine the dose-dependent neuroprotective effect of compound 5' in comparison with dihydrolipoic acid and with untreated mice, i.e. mice treated only with a vehicle but without any active ingredient.

Materials & Methods

Permanent focal cerebral ischemia in mice:

Permanent middle cerebral artery (MCA) occlusion was performed in male NMRI mice (12 to 17 animals per group) according to the method described by Welsh et al. (J. Neurochem. 1987, 846-851). Briefly, after the mice were anesthetized with tribromoethanol (600 mg/kg intraperitoneally), a small hole was drilled in the skull to expose the middle cerebral artery. The stem of the middle cerebral artery and both branches were permanently occluded by electrocoagulation. Body temperature was maintained at 37° C.±1° C. with a heating lamp during the surgical procedure. Afterwards, the mice were kept at an environmental temperature of 30° C. for 2 hours after MCA occlusion.

For histologic evaluation, the mice were anesthetized again with tribromoethanol and perfused intraperitoneally with a 1.5% solution of neutral red (0.5 ml) 2 days after middle cerebral artery occlusion. The brains were removed and stored in a fixative (4% formalin in phosphate buffer solution, pH 7.4) for 24 hours.

In this model of focal cerebral ischemia in mice, only cortical tissue was found to be infarcted, and furthermore, the infarct volume correlates with the infarct surface (C. Backhauβ et al., J. Pharmacol. Methods 1992, 27, 27-32). The tissue on the brain surface unstained by neutral red was determined (in square millimeters) as infarcted surface area by means of an image analyzing system (Kontron, Eching, Germany) according to the publication of C. Backhauβ.

The injection of compound 5', dihydrolipoic acid, and the vehicle only was performed intraperitoneally 1 hour before MCA occlusion. Compound 5' and dihydrolipoic acid were dissolved in 25% macrogol 400 (vehicle). The injected volume was always 0.25-0.30 ml per mouse. Doses of 100, 150, and 500 mg/kg compound 5' and 150 mg/kg dihydrolipoic acid were used. The control group received the vehicle (0.25-0.30 ml 25% macrogol 400 per mouse) only.

Results

The results are given as means ±SD (standard deviation). The differences between compound 5'-treated, dihydrolipoic acid-treated, and vehicle-treated animals were evaluated statistically according to the ANOVA and DUNCAN test.

In the first series of experiments it could be demonstrated that compound 5' significantly reduced the infarcted area on the mouse brain surface when administered in a concentration of 100 mg in 0.25-0.30 ml vehicle (cf. Table 6).

TABLE 6

Influence of comp. 5' and dihydrolipoic acid on infarct area after permanent MCA occlusion in NMRI mice

| Compound | Mean | SD |
| --- | --- | --- |
| 0.25-0.30 ml vehicle only | 29.89 | ±2.59 |
| 100 mg/kg comp. 5' | 26.22 | ±4.75 |
| 150 mg/kg comp. 5' | 27.00 | ±3.50 |
| 500 mg/kg comp. 5' | 28.24 | ±4.12 |
| 150 mg/kg dihydrolipoic acid | 27.94 | ±3.02 |

This effect is not clearly dose-dependent, because it seems to decrease with increasing dosage of compound 5'. Thus, it is predicted that somewhere between 20 mg/kg-100 mg/kg of compound 5' per mouse a maximum neuroprotective effect is reached. This result shows that low dosages of a compound of the present invention may be used to achieve a significant reduce of infarcted brain area.

The mean of the infarct area obtained from mice treated with 500 mg/kg compound 5' was no longer statistically reduced compared with the controls. The effect of the lowest dose of compound 5' seemed to be the most pronounced and a decrease of the neuroprotective effect was observed at higher concentrations of compound 5'. At a concentration of 500 mg/kg of compound 5' only a slight neuroprotective effect was detected while dihydrolipoic acid showed no effect at all and did not reduce the infarct area in this study.

The results discussed above clearly demonstrate the neuroprotective effect of compound 5'. In addition, the advantageous finding that a maximum neuroprotective effect is obtained at low concentrations is described. Thus, it has been proven that the compounds of the present invention can be used as anti-ischemic drugs in order to treat, for instance, stroke. Furthermore, no toxic effects could be detected in mice applied to the above-mentioned method.

Example 12

Neuroprotective Effects

This example was selected to determine the effect of the compounds of the present invention on the concentration of dopamine its metabolite 3,4-dihydroxyphenyl acetic acid (DOPAC) and 5-hydroxytryptamine (5-HT or Serotonin) and its metabolite 5-hydroxyindol acetic acid (5-HIAA) in the substantia nigra and the Striatum of Wistar rats (Charles River, Sulzbach Rosenberg).

Said two brain regions were selected in order to examine dopaminergic neurons, because it is well known that said neurons are sensitive to neurotoxines which may cause M. Parkinson, Alzheimer, and Chorea Huntington. The method as described below was used to determine degenerative processes. Sodium malonate was used as a neurotoxic substance within said method.

Materials & Methods

It is known that sodium malonate increases the release von dopamine in the Striatum of the test animals. Groups of six Wistar rats each have been used as test animals. Thus, the dopamine concentration can be used as an indicator in order to determine the harmful effect of neurotoxines.

100 mg of compound 5' were dissolved in 5 ml 50% propan-1,2-diol (Merck, Darmstadt). Four 5 ml portions of compound 5' were administered intraperitoneal to the test animals. The first portion was administered in the evening of the first test day, the second portion during the next morning, the third portion in the evening of the second test day and the late portion during the morning of the third test day. Thirty minutes after the last application of compound 5' 2 μmol sodium malonate dissolved in physiologic sodium chloride solution were injected into the left Striatum by means of a precision pump (flow rate 0.5 μl/min.) after having anesthetized the rats (Ketamin: 80 mg/kg and Xylasin: 6-10 mg/kg).

Four days after sodium malonate application, the Striatum and the treated and untreated part of the substantia nigra was separately excised, weighted, homogenized with perchloric acid, and centrifuged. Aliquots of the supernatants were subsequently subjected to HPLC and by the means of HPLC-ELCD the amount of dopamine, DOPAC, 5-HT, 5-HIAA, and 3-methoxytyramine was calorimetrically measured.

Results

The application of sodium malonate leads to a reduction of dopamine and its metabolites HVA and DOPAC. The neurotoxin malonate decreased the concentration of dopamine (−44%, p<0.001) and of DOPAC (−30%, p<0.001). Compound 5' is able to increase the concentration of dopamine (+18%, p<0.05) and of DOPAC (+10%, p<0.05) in the Striatum. Furthermore, it could be demonstrated that the application of malonate together with compound 5' did not lead to such a dramatic decrease in dopamine and DOPAC concentration. The additional application of compound 5' compensated the malonate effect (+44% more dopamine in comparison to the application of malonate only) (cf. FIG. 4).

Furthermore, it could be shown that administration of the compound 5' increased dramatically the level of 5-HT and its metabolite 5-HIAA (cf. FIG. 5a and 5b). In cases of reduced levels of 5-HT and 5-HIAA, administration of compound 5' was able to significantly increase 5-HT and 5-HIAA levels to normal values. Thus, administration of compound 5' compensates or over-compensates the diminishing effect on the 5-HT and 5-HIAA levels.

The results exhibited above clearly demonstrate the neuroprotective effect of compound 5'. The advantageous findings show that compound 5' is capable of compensating the harmful effect of neurotoxins and is able to increase the 5-HT and 5-HIAA levels. Thus, it has been proven that the compounds of the present invention can be used as drugs in order to treat, for instance, Parkinson, Alzheimer, Chorea Huntington or depression.

The invention claimed is:

1. A method for treating at least one disease or condition selected from the group consisting of diabetes mellitus Type I and Type II, heavy metal poisoning, cerebral iseliemic disease, depression and stroke, in a mammal, said method comprises:

administering to said mammal an amount of at least one compound of the general formula (I) and/or pharmaceutically acceptable salts thereof effective to treat the disease or condition:

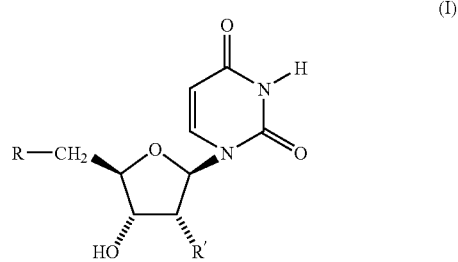

wherein

R represents R"—COO; and

R' represents hydrogen or a hydroxy group;

wherein R" represents a monoenoic alkyl chain with 10 to 24 carbon atoms, a monoenoic branched alkyl chain with 10 to 24 carbon atoms, a polyenoic alkyl chain with 10 to 24 carbon atoms, a polyenoic branched alkyl chain with 10 to 24 carbon atoms, a branched or unbranched alkyl chain with 8 to 20 carbon atoms containing a carbocyclic or heterocyclic ring, a monoynoic alkyl chain with 10 to 24 carbon atoms, a monoynoic branched alkyl chain with 10 to 24 carbon atoms, a polyynoic alkyl chain with 10 to 24 carbon atoms, a polyynoic branched alkyl chain with 10 to 24 carbon atoms.

2. The method according to claim 1, wherein at least one compound of the general formula (I) and/or pharmaceutically acceptable salts thereof is administered intravenously, intraperitoneally, intramuscularly, subcutaneously, mucocutaneously, orally, rectally, transdermally, topically, intradermally, intragastrally, intracutaneously, intravaginally, intravasally, intranasally, intrabuccally, percutaneously, sublingually, or by inhalation.

3. The method according to claim 1, wherein said mammal is a human.

4. The method according to claim 1, wherein R" represents cis-9 tetradecenyl, cis-9-hexadecenyl, cis-6-octadecenyl, cis-9-octadecenyl, cis-11-octadecenyl, cis-9-eicosenyl, cis-11-eicosenyl, cis-13-docosenyl, cis-15-tetracosenyl, 9,12-octadecadienyl, 6,9,12-octadecatrienyl, 8,11,14-eicosatrienyl, 5,8,11,14-eicosatetraenyl, 7,10,13,16-docosatetraenyl, 4,7,10,13,16 docosapentaenyl, 9,12,15-octadecatrienyl, 6,9,12,15-octadecatetraenyl, 8,11,14,17-eicosatetraenyl, 5,8,11,14,17-eicosapentaenyl, 7,10,13,16,19-docosapentacnyl, 4,7,10,13,16,19-docosahexaenyl, 5,8,11-eicosatrienyl, 1,2-dithiolane-3-pentanyl, 6,8-dithiane octanyl, docosaheptadecanyl, eleostearyl, calendyl, catalpyl, taxoleyl, pinolenyl, sciadonyl, retinyl, 14-methyl pentadecanyl, pristanyl, phytanyl, 11,12-methyleneoctadecanyl, 9,10-methylenehexadecanyl, 9,10-epoxystearyl, 9,10-epoxyoctadec-12-enyl, 6-octadecynyl, t11-octadecen-9-ynyl, 9-octadecynyl, 6-octadecen-9-ynyl, t10-heptadecen-8-ynyl, 9-octadecen-12-ynyl, t7,t11-octadecadiene-9-ynyl, t8,t10-octadecadiene-12-ynyl, 5,8,11,14-eicosatetraynyl, 2-hydroxytetracosanyl, 2-hydroxy-15-tetracosenyl, 12-hydroxy-9-octadecenyl or 14-hydroxy-11-eicosenyl.

5. The method according to claim 1 or 4, wherein the compound of the general formula (I) and/or pharmaceutically acceptable salts thereof is administered in a daily dosage corresponding to an effective concentration in the range of 1-10000 mg.

6. The method according to claim 5, wherein the compound of the general formula (I) and/or pharmaceutically acceptable salts thereof is administered in a daily dosage corresponding to an effective concentration in the range of 1-5000 mg.

7. The method according to claim 6, wherein the compound of the general formula (I) and/or pharmaceutically acceptable salts thereof is administered in a daily dosage corresponding to an effective concentration in the range of 10-1000 mg.

* * * * *